(12) United States Patent
McGuinn et al.

(10) Patent No.: US 12,678,282 B2
(45) Date of Patent: Jul. 14, 2026

(54) TRANSCATHETER PROSTHETIC HEART VALVE DELIVERY SYSTEM WITH DISTAL CUTTING ASSEMBLY

(71) Applicant: Medtronic Vascular, Inc., Santa Rosa, CA (US)

(72) Inventors: Alan McGuinn, Oranmore (IE); Paul Devereux, Tuam (IE); Brendan Vaughan, Miltown Malbay (IE); David O'Toole, Oranmore (IE); Padraigh Jennings, Summerhill (IE); Michael Walsh, Oaklands (IE); Stephen Montgomery, Galway (IE); Ronja Pfeiffer, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 28 days.

(21) Appl. No.: 18/810,470

(22) Filed: Aug. 20, 2024

(65) Prior Publication Data

US 2024/0407922 A1     Dec. 12, 2024

Related U.S. Application Data

(62) Division of application No. 17/870,925, filed on Jul. 22, 2022, now Pat. No. 12,097,117, which is a
(Continued)

(51) Int. Cl.
| | |
|---|---|
| *A61F 2/24* | (2006.01) |
| *A61F 2/95* | (2013.01) |
| *A61B 17/04* | (2006.01) |

(52) U.S. Cl.
CPC .............. *A61F 2/2439* (2013.01); *A61F 2/95* (2013.01); *A61B 17/0467* (2013.01); *A61F 2002/9511* (2013.01); *A61F 2/9517* (2020.05)

(58) Field of Classification Search
CPC ........ A61F 2/2439; A61F 2/9517; A61F 2/95; A61F 2002/9511; A61B 17/0467
See application file for complete search history.

(56) References Cited

U.S. PATENT DOCUMENTS

| | | | |
|---|---|---|---|
| 8,109,986 | B2 | 2/2012 | Styrc |
| 8,911,461 | B2 | 12/2014 | Traynor et al. |
| | | (Continued) | |

FOREIGN PATENT DOCUMENTS

| | | |
|---|---|---|
| CN | 102125470 | 7/2011 |
| CN | 102166143 | 8/2011 |
| | (Continued) | |

*Primary Examiner* — Anh T Dang
(74) *Attorney, Agent, or Firm* — Wentsler LLC

(57) ABSTRACT

The disclosure relates to transcatheter stented prosthesis delivery devices including a handle assembly connected to a shaft assembly on which a stented prosthesis is loaded and compressively retained with a plurality of elongate tension members. The delivery devices include a cutting assembly that can sever the elongate tension members after the stented prosthesis is expanded at a target site so that the delivery device can be withdrawn from the patient. Certain embodiments position the cutting assembly at least within the shaft assembly and others position the cutting assembly over the shaft assembly. Various disclosed cutting assemblies are actuated with the handle assembly or the like, which draw the tension members across the blade or vice versa.

20 Claims, 18 Drawing Sheets

Related U.S. Application Data division of application No. 16/038,539, filed on Jul. 18, 2018, now Pat. No. 11,426,277.

(60) Provisional application No. 62/534,043, filed on Jul. 18, 2017.

(56)                References Cited

U.S. PATENT DOCUMENTS

| | | | |
|---|---|---|---|
| 8,920,459 B2 | 12/2014 | Lorenzo | |
| 10,004,599 B2 | 6/2018 | Rabito et al. | |
| 10,368,989 B2 | 8/2019 | Duffy et al. | |
| 10,905,551 B2 | 2/2021 | Cunningham et al. | |
| 2002/0029076 A1* | 3/2002 | Yee | A61F 2/966 |
| | | | 606/108 |
| 2002/0165569 A1 | 11/2002 | Ramzipoor et al. | |
| 2009/0132037 A1 | 5/2009 | Hoffman et al. | |
| 2012/0136378 A1 | 5/2012 | Snell et al. | |
| 2012/0253471 A1 | 10/2012 | Tully et al. | |
| 2014/0330368 A1* | 11/2014 | Gloss | A61F 2/243 |
| | | | 623/2.11 |
| 2016/0250051 A1 | 9/2016 | Lim et al. | |
| 2019/0021858 A1 | 1/2019 | McGuinn et al. | |

FOREIGN PATENT DOCUMENTS

| | | |
|---|---|---|
| CN | 106943207 | 7/2017 |
| WO | 2013118352 | 8/2013 |
| WO | 2014164302 | 10/2014 |
| WO | 2017160756 | 9/2017 |
| WO | 2017218877 | 12/2017 |

* cited by examiner

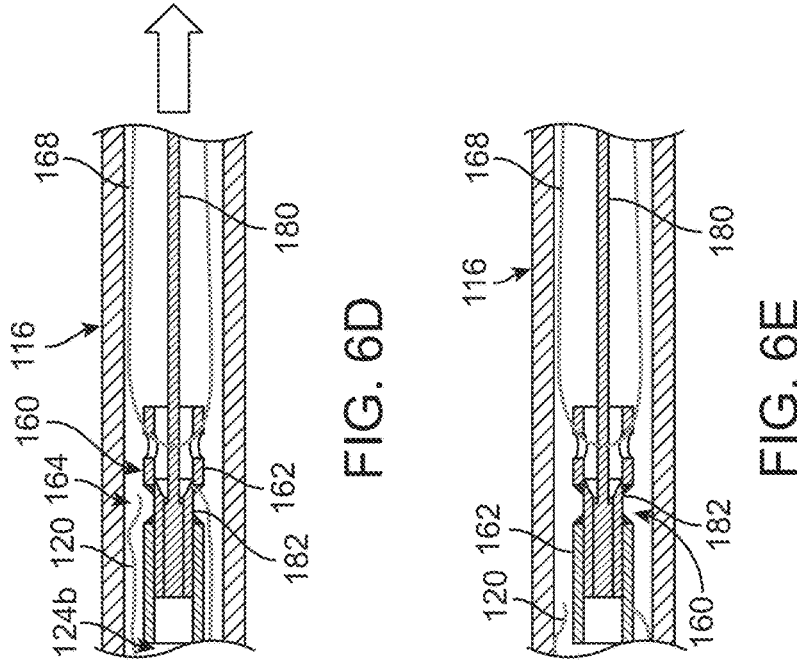
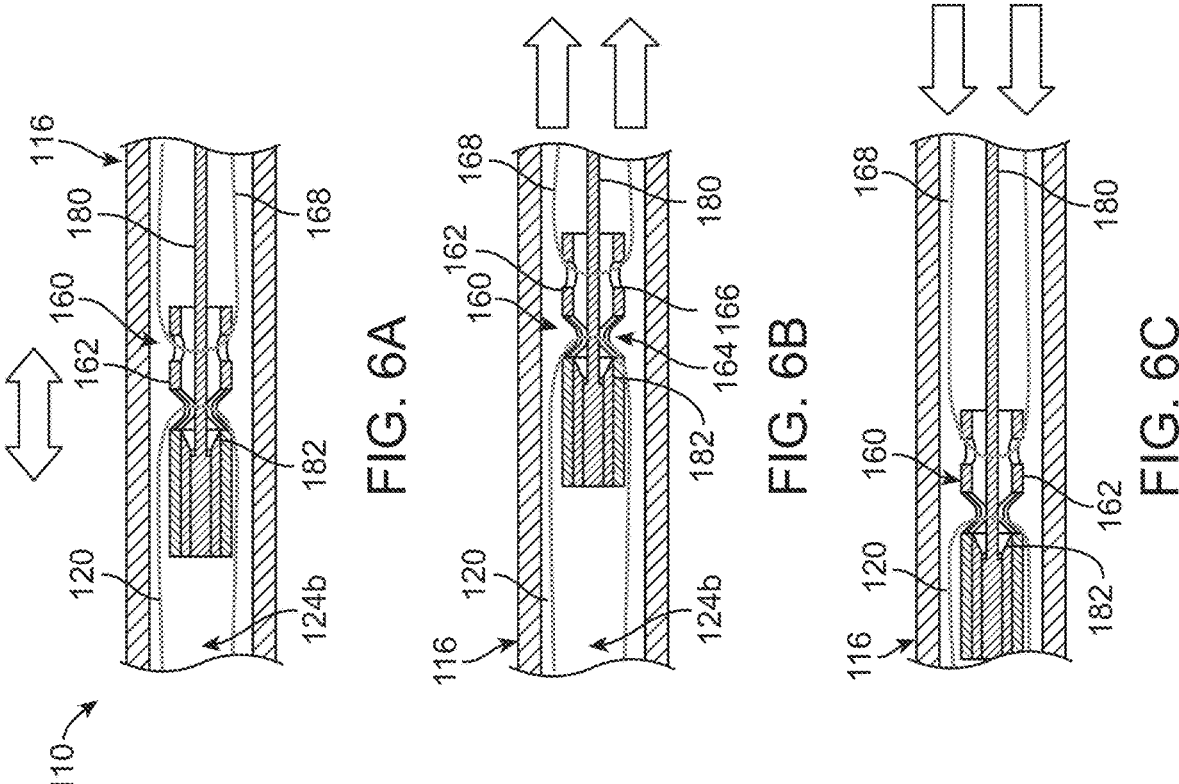

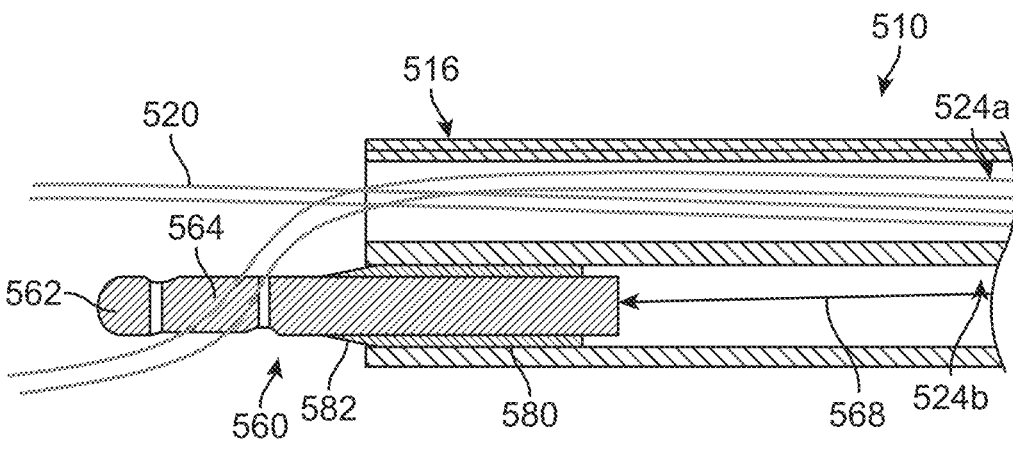
FIG. 10A
FIG. 10B
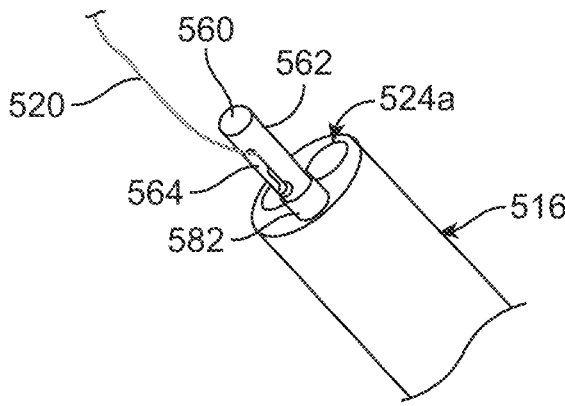
FIG. 11

TRANSCATHETER PROSTHETIC HEART VALVE DELIVERY SYSTEM WITH DISTAL CUTTING ASSEMBLY

CROSS-REFERENCE TO RELATED APPLICATIONS

This application is a divisional of U.S. application Ser. No. 17/870,925, filed Jul. 22, 2022, which is a divisional of U.S. application Ser. No. 16/038,539, filed Jul. 18, 2018, now U.S. Pat. No. 11,426,277, which claims the benefit of U.S. Provisional Application No. 62/534,043, filed Jul. 18, 2017, the entire contents of each application which are incorporated herein by reference.

BACKGROUND

The present disclosure relates to transcatheter stented prosthesis delivery devices that utilize one or more elongate tension members to compressively retain a stented prosthesis to the delivery device.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The present disclosure addresses improvements related to the above.

SUMMARY

The present disclosure relates to numerous delivery devices for transcatheter stented prosthesis (e.g., a stented prosthetic heart valve) loading, delivery and implantation. Such delivery devices can include an optional outer delivery sheath assembly, a shaft assembly and a handle assembly. The delivery device provides a loaded delivery state in which the stented prosthesis is loaded and compressed over a distal portion of the shaft assembly. Compression of the stented prosthesis is adjustable with one or more elongate tension members, which extend around the stented prosthesis and proximately to an actuator that can optionally be located in the handle assembly. The delivery device can be manipulated to adjust tension in the tension members to permit the stented prosthesis to self-expand, contract and ultimately release from the shaft assembly.

Partial or full compression of the stented prosthesis is achieved by pulling or otherwise retracting the tension members proximally. The present inventors have observed that with some tension member routing configurations where only one end of teach tension member is pulled, compression of the stented prosthesis is uneven about its circumference. In embodiments where both ends of each tension member are pulled to more uniformly compress the stented prosthesis, the tension members can become tangled, damaged or otherwise caught as the tension members are pulled over the stented prosthesis and through the delivery device for removal after deployment of the stented prosthesis. Therefore, aspects of the present disclosure relate delivery devices having cutting assemblies positioned near the stented prosthesis so that the tension members can be severed proximate the stented prosthesis for easier removal of the tension members after the stented prosthesis is deployed.

BRIEF DESCRIPTION OF THE DRAWINGS

FIG. 1 is a perspective view of an example of a delivery device for delivering a stented prosthetic heart valve or the like.

FIG. 6A is a partial, schematic illustration indicating that the cutting assembly of FIGS. 5A-5B can slide within a lumen of the shaft assembly.

FIG. 6B is a partial, schematic illustration of the cutting assembly of FIGS. 5A-6A being pulled proximally with a pull member to compress the stented prosthesis (not shown).

FIG. 6C is a partial, schematic illustration of the cutting assembly of FIGS. 5A-6B moving distally as tension in the pull member is released to allow the stented prosthesis to expand (not shown).

FIG. 6D is a partial, schematic illustration of the cutting assembly of FIGS. 5A-6C illustrating the tension member being severed with the cutting assembly.

FIG. 6E is a partial, schematic illustration of the cutting assembly of FIGS. 5A-6D after the tension member is severed with the cutting assembly.

FIG. 10A is a partial, schematic illustration of an alternate delivery device prior to actuation of a cutting assembly.

FIG. 10B is a partial, schematic illustration of the delivery device of FIG. 10A after actuation of the cutting assembly.

FIG. 11 is a partial, perspective view of the cutting assembly and shaft assembly of the delivery device of FIGS. 10A-10B.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
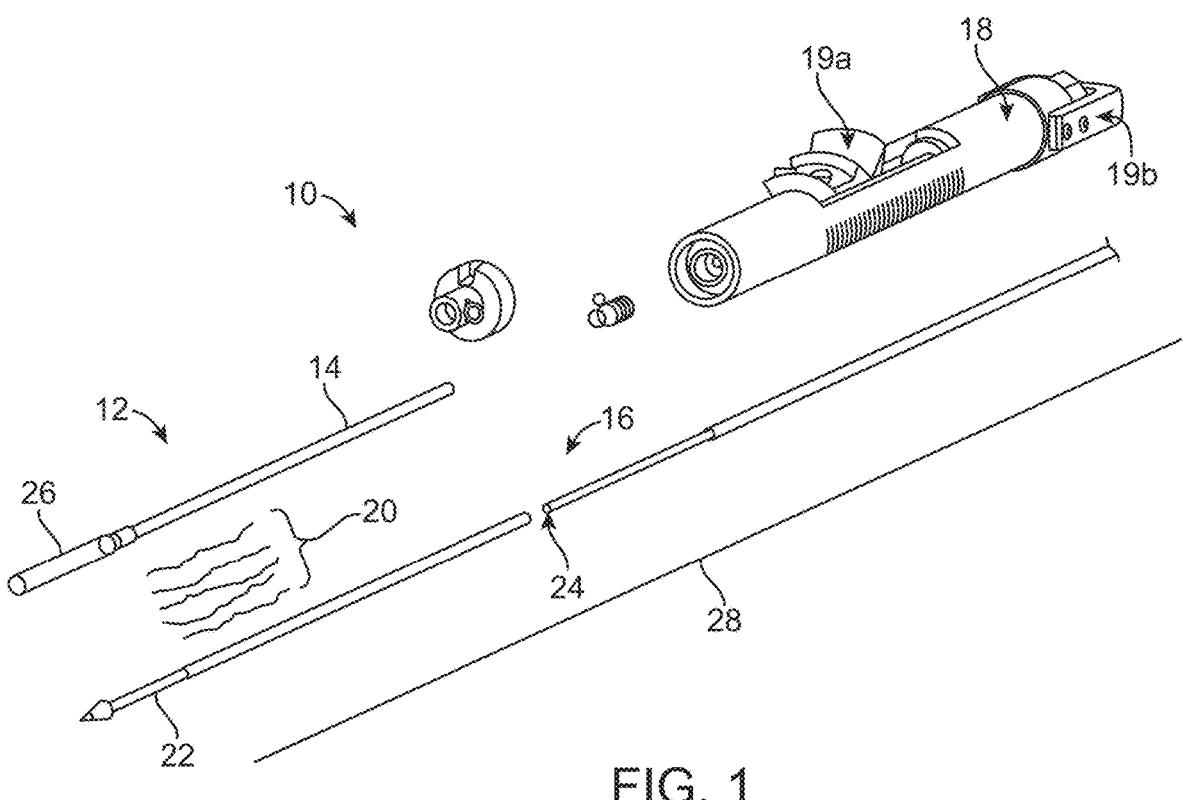
Figure 2A:
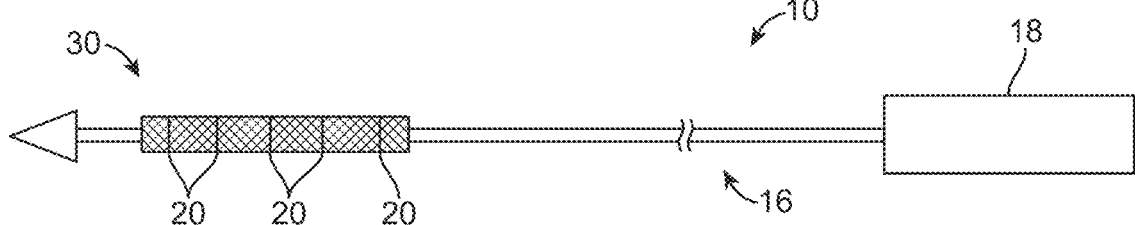
FIG. 2A is a schematic illustration of the delivery device of FIG. 1 having the stented prosthetic heart valve positioned over a distal portion of the delivery device with a plurality of elongate tension members in a compressed arrangement.
Figure 2B:
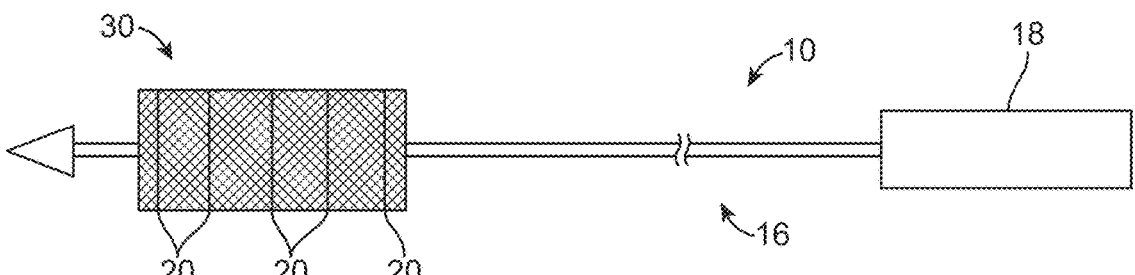
FIG. 2B is a partial, schematic illustration of the delivery device of FIG. 2A having the stented prosthetic heart valve positioned over the distal portion; wherein the stented prosthetic heart valve is shown in an expanded arrangement.
Figure 3:
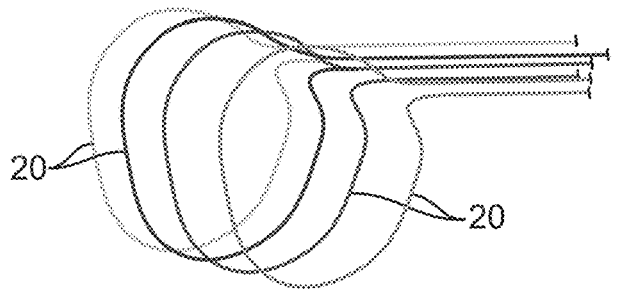
FIG. 3 is a schematic illustration of how elongate tension members can be routed around a stented prosthesis (the stented prosthesis is omitted for ease of illustration).

As described below, some aspects of the present disclosure relate to delivery devices utilizing one or more tension members to compress and retain a stented prosthesis to the delivery device during transcatheter delivery to a target site. By way of background, general components of one non-limiting example of a delivery device 10 with which some aspects of the present disclosure are useful are illustrated in FIGS. 1-3. The delivery device 10 is arranged and configured for percutaneously delivering a stented prosthesis, such as a stented prosthetic heart valve 30 (schematically illustrated), to a target site. The delivery device 10 includes an optional outer sheath assembly 12 having a flexible outer sheath 14, a flexible shaft assembly 16 and a handle assembly 18. The shaft assembly 16 can include a distal portion 22 having one or more apertures (not shown) for receiving the tension members 20. The shaft assembly 16 can further define one or more continuous lumens 24 (referenced generally) sized to slidably receive an auxiliary component such as a guide wire 28 and/or one or more tension members 20. In this embodiment, the outer sheath 14 is interconnected to a capsule 26 that is selectively disposed over the stented prosthesis 30 and assists in constraining the stented prosthesis 30. The capsule 26 can be retracted by the handle assembly 18 to expose the stented prosthesis 30 for deployment.

One or more elongate tension members 20 (e.g., sutures, cords, wires or filaments) are further provided, and can be considered part of the delivery device 10 in some embodiments or as part of the stented prosthesis 30 in other embodiments. Some examples in which the tension members 20 can be arranged are schematically illustrated in FIGS. 2A-3 (the stented prosthesis and other delivery device components being omitted in FIG. 3 for ease of illustration). One end of each of the tension members 20 can be secured proximate the handle assembly 18, then each tension member 20 can extend distally to wrap around the stented prosthesis 30 positioned over the distal portion 22 and then back to the handle assembly 18 or other mechanism for maintaining and adjusting the desired level of tension in the tension members 20 either individually or in pairs or groups of tension members 20. Other tension member arrangements are envisioned. The delivery device 10 provides a loaded, compressed arrangement (FIG. 2A) in which the stented prosthesis 30 is loaded over the shaft assembly 16 and is compressively retained on the distal portion 22 by the tension members 20 and optionally the capsule 26. As is schematically illustrated in FIGS. 2A-2B, compression of the stented prosthesis 30 is adjustable with the tension members 20. In this illustrated embodiment, the tension members 20 wrap around the stented prosthesis 30 normal to an axis of the shaft assembly 16. Alternatively, the tension members 20 can be configured to wrap around the stented prosthesis 30 at other angles with respect to the axis of the shaft assembly 16.

The handle assembly 18 can include one or more actuators 19a, 19b. The actuators 19a, 19b can be arranged and configured to accomplish a variety of functions. For example, the first actuator 19a can be operated to proximally retract the capsule 26 and expose the stented prosthesis 30 relative to the capsule 26. The second actuator 19b can be operated to adjust tension in the tension members 20 to compress or expand the stented prosthesis 30, for example.

After being loaded, compressed and optionally sheathed with the capsule 26, the stented prosthesis 30 is delivered to the native defective heart valve or other target site. Once the stented prosthesis 30 is sheathed with the capsule 26, tension in the tension members 20 can be released (e.g., via actuator 19b), if desired, as the capsule 26 maintains the stented prosthesis 30 in the compressed arrangement. Once in position, the capsule 26 is retracted (if provided) and/or tension in the tension members 20 is lessened or released to permit the stented prosthesis 30 to self-expand to an expanded arrangement, partially releasing and ultimately fully deploying the stented prosthesis 30 from the shaft assembly 16 (see, FIG. 2B). Then, one end of each of the tension members 20 can be released from the delivery device 10 so that the other end of each of the tension members 20 can be pulled proximally, thus pulling the free end of each tension member 20 from the stented prosthesis 30 to be withdrawn from the patient along with the delivery device 10. In alternate embodiments, as discussed in more detail below, the tension members 20 can be cut for release from around the stented prosthesis 30. It is to be understood that the specific configuration of the delivery device 10 disclosed above is provided as only one example and that aspects of the disclosure can also be used with other types of delivery devices.

As referred to herein, the stented prostheses and stented prosthetic heart valves or "prosthetic valves" useful with the various devices and methods of the present disclosure may assume a wide variety of configurations. The prosthetic valves can include a bioprosthetic heart valve having tissue leaflets or a synthetic heart valve having polymeric, metallic or tissue-engineered leaflets, and can be specifically configured for replacing valves of the human heart. The stented prosthesis and prosthetic valves of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 4A:
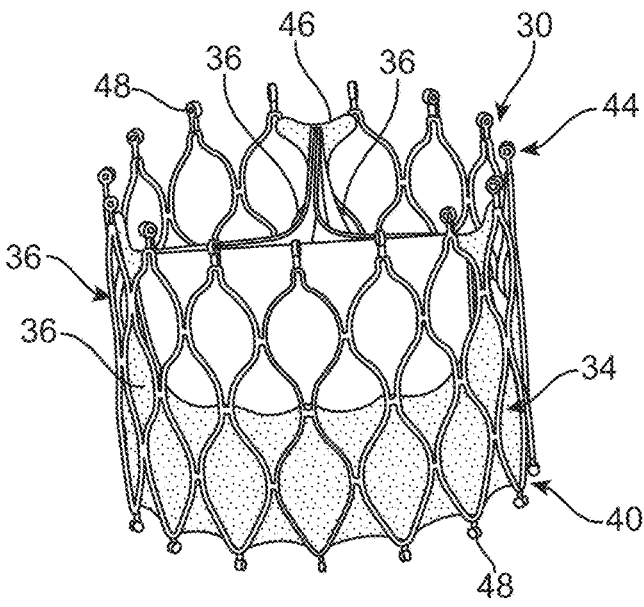
FIG. 4A is a perspective view of one stented prosthetic heart valve that can be used with the delivery devices disclosed herein shown in the expanded arrangement.
Figure 4B:
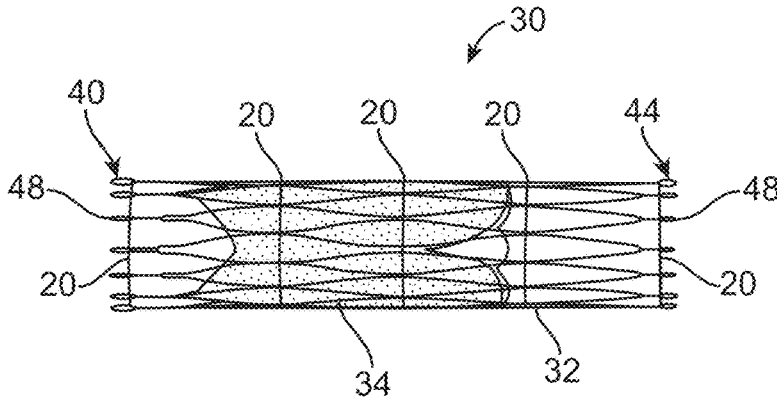
FIG. 4B is a front view of the stented prosthesis of FIG. 4A in the compressed arrangement.
Figure 5A:
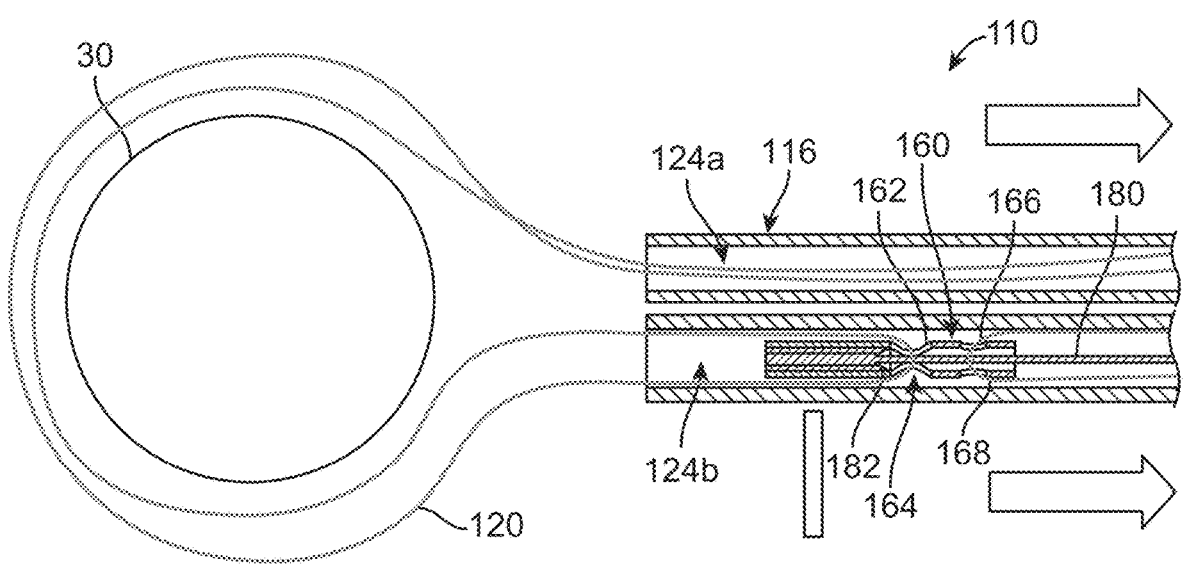
FIG. 5A is a partial, schematic illustration of a distal portion of a delivery device having a cutting assembly for severing a plurality of tension members.
Figure 5B:
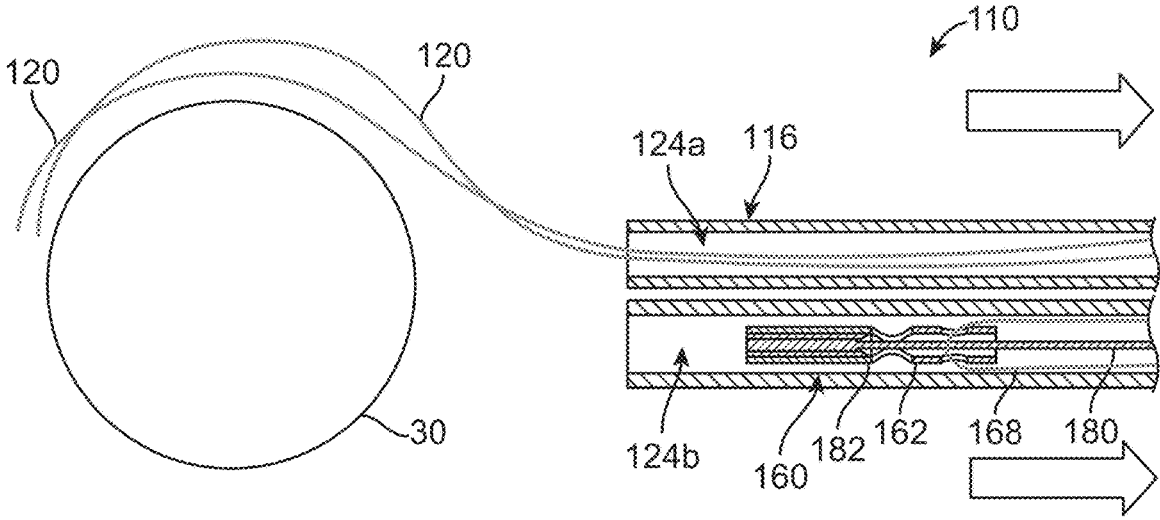
FIG. 5B is a partial, schematic illustration of the distal portion of the delivery device of FIG. 5A after actuation of the cutting assembly.

One non-limiting example of the stented prosthesis 30 is illustrated in detail in FIGS. 4A-4B. As a point of reference, the stented prosthesis 30 is shown in a normal or expanded arrangement in the view of FIG. 4A and a compressed arrangement in FIG. 4B. The stented prosthesis 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the stented prosthesis 30 can be achieved with one or more elongate tension members 20.

If provided, the valve structure 34 of the stented prosthesis 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 4A-4B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The stented prosthesis 30 includes a first end 40 and an opposing second end 44 of the stented prosthesis 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around the stent frame 32 (only one post 46 is clearly visible in FIG. 4A).

Turning now also to FIGS. 5A-6E, which schematically illustrate one alternate delivery device 110 that is identical to delivery device 10 unless explicitly stated. The delivery device 110 has a shaft assembly 116 (e.g., similar to the shaft assembly 16 and the delivery device 10). The shaft assembly 116 of this embodiment can include two lumens 124a, 124b for each tension member 120 provided (only one pair of lumens 124a, 124b is shown for ease of illustration). To selectively release one respective tension member 120 from the stented prosthesis 30, the delivery device 110 includes a cutting assembly 160 that is slidably positioned within the second lumen 124b of the shaft assembly 116 (FIG. 6A).

The cutting assembly 160 includes a hollow blade holder 162 having first and second apertures 164, 166. The cutting assembly 160 also provides a pull member 168 that is at least partially positioned within the second aperture 166 of the blade holder 162 for moving the blade holder 162 within the second lumen 124b. The pull member 168 can be made of a similar material as compared to the tension member(s) 120, for example. The cutting assembly 160 further includes handle actuator 180 at least partially positioned within the blade holder 162 and interconnected to a blade 182. In some embodiments, the handle actuator 180 extends through the second lumen 124b to the handle assembly so that an actuator of the handle assembly can control movement of the handle actuator 180 and thus, movement of the blade 182 (examples of a suitable handle assembly and actuators are described above and shown in FIG. 1).

Each tension member 120 is threaded from the handle assembly, distally through the first lumen 124a, around the stented prosthesis 30, proximally through the second lumen 124b, then through the first aperture 164 and then back distally out of the second lumen 124b, around the stented prosthesis 30, and then back proximally through the first lumen 124a to the handle assembly. In alternate embodiments, the shaft assembly 116 can include a plurality of shafts of the type shown in FIGS. 6A-6D), each shaft assembly having at least two lumens for one respective tension member 120.

In various embodiments, the handle assembly is configured to draw the cutting assembly 160 proximally to correspondingly pull the tension member 120 to compress the stented prosthesis (FIG. 6B). The handle actuator 180 can also be pushed proximally to release compression on the stented prosthesis 30 so that the stented prosthesis 30 expands for deployment (FIG. 6C). When compressive force on the stented prosthesis is released (e.g., via releasing tension applied to the handle actuator 180), the tension members 120 will correspondingly draw the cutting assembly 160 distally as the stented prosthesis 30 naturally expands. After deployment of the stented prosthesis 30, the pull member 168 is pulled proximally sufficiently to draw the blade 182 against and past the tension member 120, effectively severing the tension member (FIG. 6D). Then, the tension member 120 is released from being secured around the stented prosthesis 30 so that the delivery device 110 and the tension member 120 can be withdrawn from the patient (FIG. 6E). As indicated above, respective shafts and/or lumen pairs can be provided for each tension member used to compress the stented prosthesis, which can prevent tangling of the tension members. In alternate various embodiments, the blade holder 162 can be attached to and considered a component of a rigid shaft, provided alongside handle actuator 180 as a replacement to pull member 168. In this configuration, the rigid shaft (and thus the blade holder 162) can be held stationary as the handle actuator 180 is pulled proximally to bring the blade 182 in contact with the tension member 120 (i.e. during the severing/cutting action). By holding the blade holder 162 in place and maintaining a longitudinal position of the blade holder 162 with respect to the shaft assembly 116, the force of the blade 182 will not pull the tension member 120 and blade holder 162 during the severing or cutting step. For the specific embodiment shown in FIGS. 6A-6D, movement of the blade holder 162 during the severing step (FIG. 6D) will be less likely as the sharpness of the blade 182 increases.

Figures 7A, 7B:
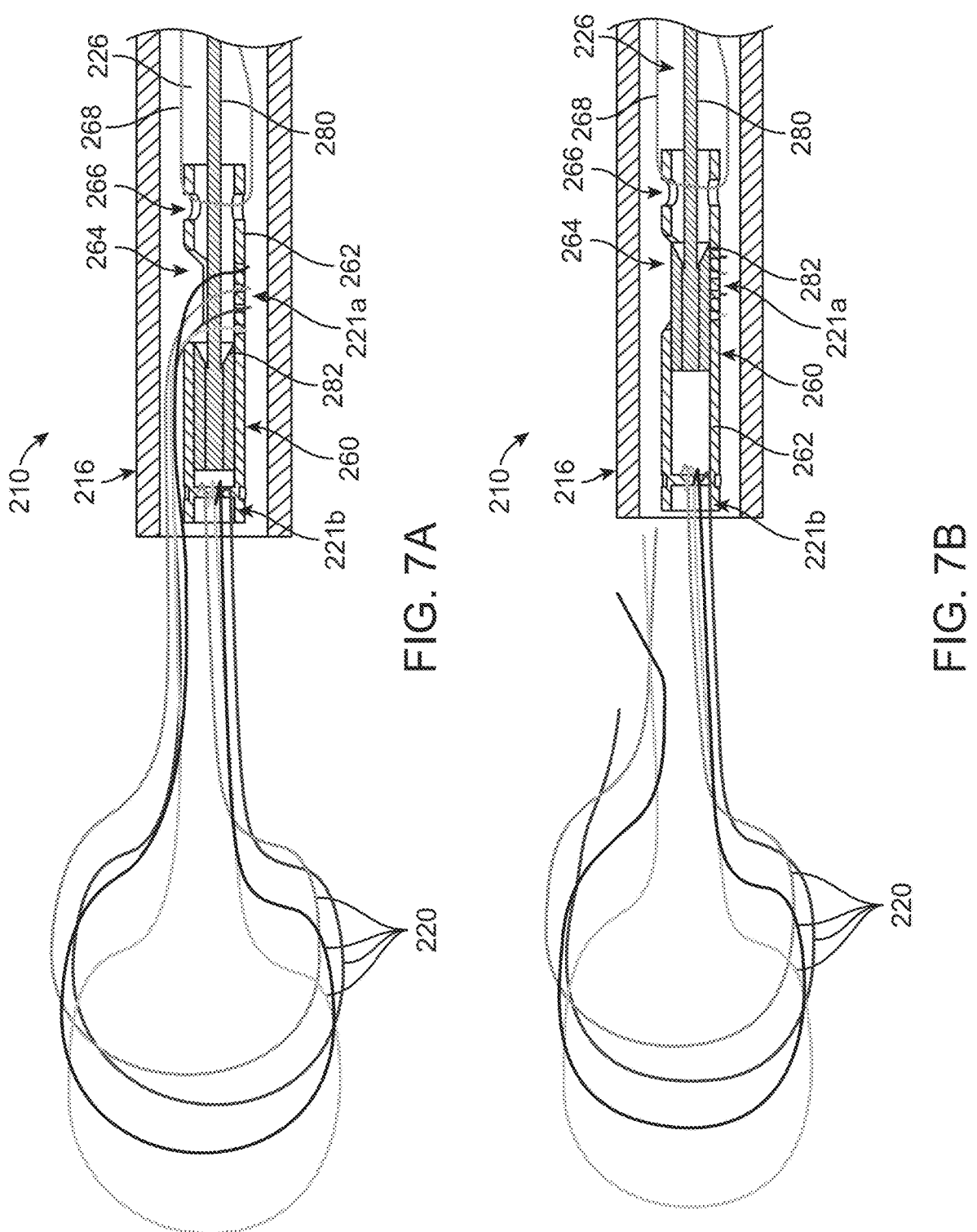
FIG. 7A is a partial, schematic illustration of select components of an alternate delivery device prior to actuation of a cutting assembly.
FIG. 7B is a partial, schematic illustration of the delivery device of FIG. 7A after actuation of the cutting assembly.

Turning now also to FIGS. 7A-7B, which schematically illustrate select components of a similar embodiment of a delivery device 210 that is identical to delivery device 10 unless explicitly stated. The delivery device 210 includes a shaft assembly 216 having at least one lumen 226, a cutting assembly 260 and a plurality of tension members 220 that can be used to control compression of a stented prosthesis (not shown; see, e.g., FIGS. 1-2B and related disclosure) retained on the shaft assembly 216. The cutting assembly 260 includes a blade holder 262 connected to a pull member 268 and a handle actuator 280 connected to a blade 282. The blade holder 262 has first and second apertures 264, 266.

In this embodiment, both ends 221a, 221b (referenced generally) of each tension member 220 are initially connected to the cutting assembly 260 (FIG. 7A). One end 221a of each tension member 220 can comprise a loop through which the handle actuator 280 is threaded. The other end 221b of each tension member 220 can be tied or otherwise secured to the blade holder 262. It is envisioned that the second end 221b of the tension members 220 can be secured in other locations on the blade holder 262. In this arrangement, the pull member 268 is configured to tension each tension member 220 upon proximal retraction of the pull member 268, and thus the blade holder 262, via a handle assembly or the like (see, e.g., the handle assembly 18 of FIG. 1). The handle actuator 280 is configured to selectively actuate movement of the blade 282 to sever the tension members 220. Movement of the handle actuator 280 can be controlled with the handle assembly, for example. As the blade 282 is moved proximally, via the handle actuator 280 or the like within the blade holder 262, the blade 282 is directed over and severs the tension members 220 (FIG. 7B) at the first end 221a. The tension members 220 remain connected to the delivery device 210 at their respective second ends 221b and can therefore be pulled by proximal movement of the shaft assembly 216 and the blade holder 262 to release the tension members 220 from the stented prosthesis and withdraw the tension members 220 from the patient. All other elements of the delivery device 210 can be configured and operate in ways similar to those disclosed with respect to other embodiments.

Figure 8A:
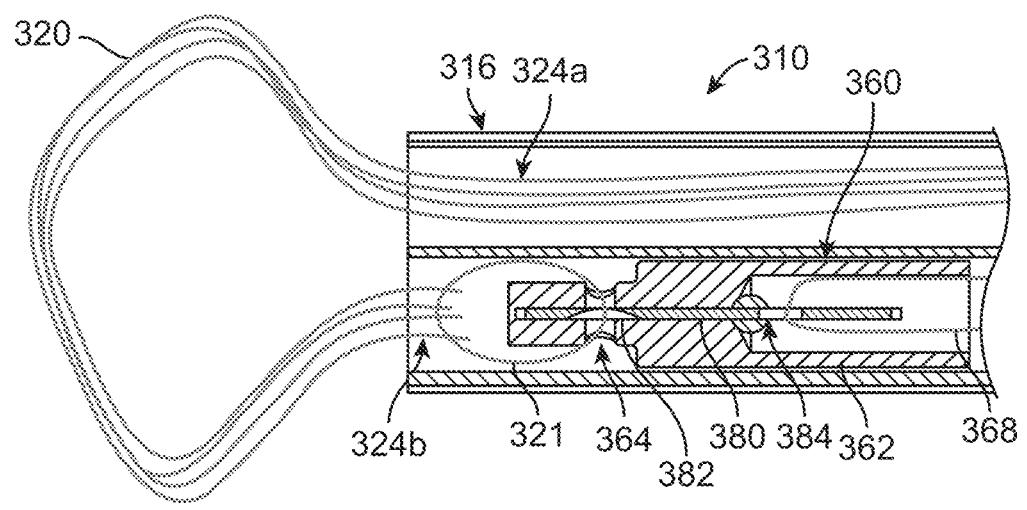
FIG. 8A is a partial, schematic illustration of an alternate delivery device prior to actuation of a cutting assembly.
Figure 8B:
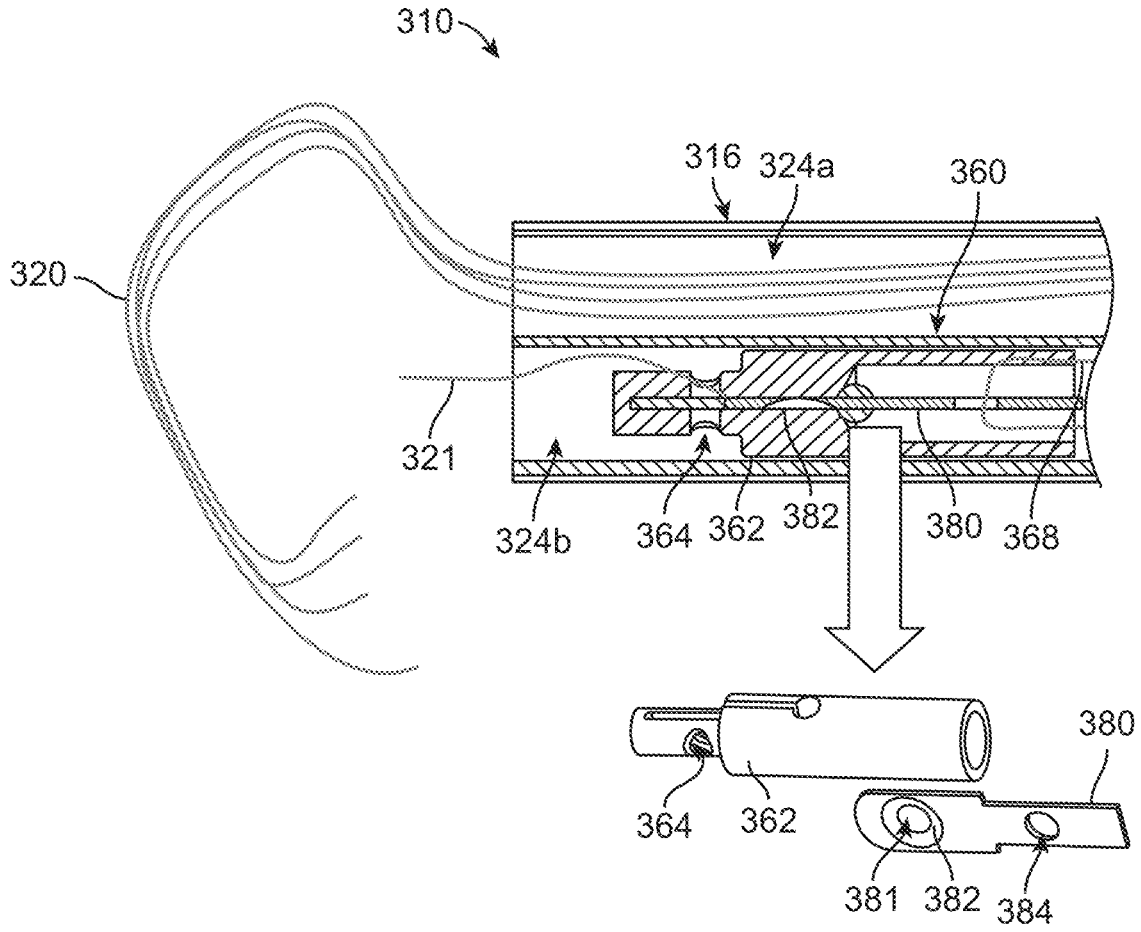
FIG. 8B is a partial, schematic illustration of the delivery device of FIG. 8A after actuation of the cutting assembly.

In a similar embodiment of a delivery device 310, select components of which are schematically shown in FIGS. 8A-8B, the delivery device 310 includes a shaft assembly 316 having two lumens 324a, 324b and a cutting assembly 360. The cutting assembly 360 has a blade holder 362, a cutting plate 380, which is planar and has a circular aperture 381 around which a blade 382 is formed. This configuration allows for the cutting plate 380 to be shorter as compared to the handle actuator 280 of FIGS. 7A-7B. This embodiment is similar to those shown above except as explicitly stated. At least one tension member 320 (generally referenced) of the type disclosed above (generally referenced) are each threaded through the first lumen 324a of the shaft assembly 316 and around the stented prosthesis (the stented prosthesis is not shown for ease of illustration). The tension members 320 are joined with a loop 321 that is positioned through both an aperture 364 in the blade holder 362 and the aperture 381 of the cutting plate 380. A pull member 368 of the type disclosed above (e.g., the pull member 168) is connected to the cutting plate 380 and can be pulled proximally to draw the loop 321 against the blade 382, thus severing the loop 321 and disconnecting the tension members 320 from the blade holder 362 so that the tension members 320 can be pulled from around the stented prosthesis and proximally withdrawn from the patient with the delivery device 310. In one example embodiment, the blade holder 362 includes an aperture 384 through which the pull member 368 is threaded. The delivery device 310 is otherwise identical to delivery device 10.

Figure 9A:
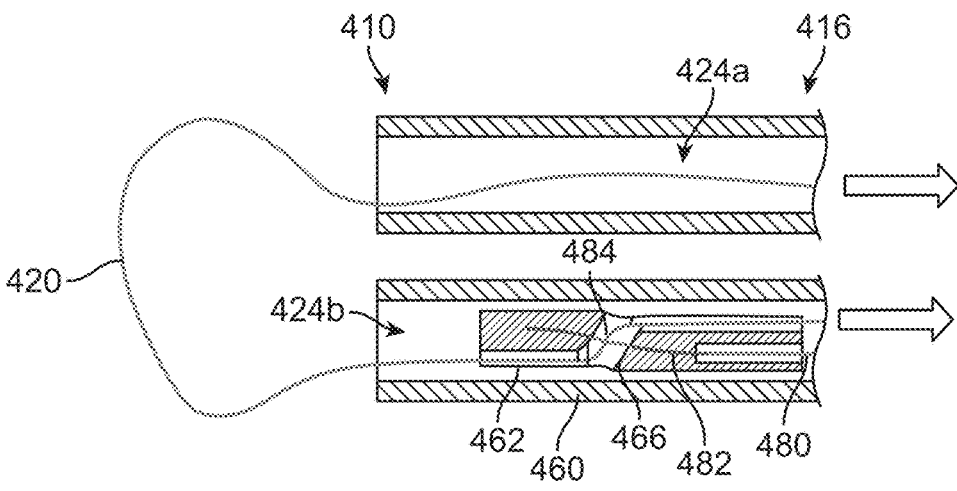
FIG. 9A is a partial, schematic illustration of select components of an alternate delivery device prior to actuation of a cutting assembly.
Figure 9B:
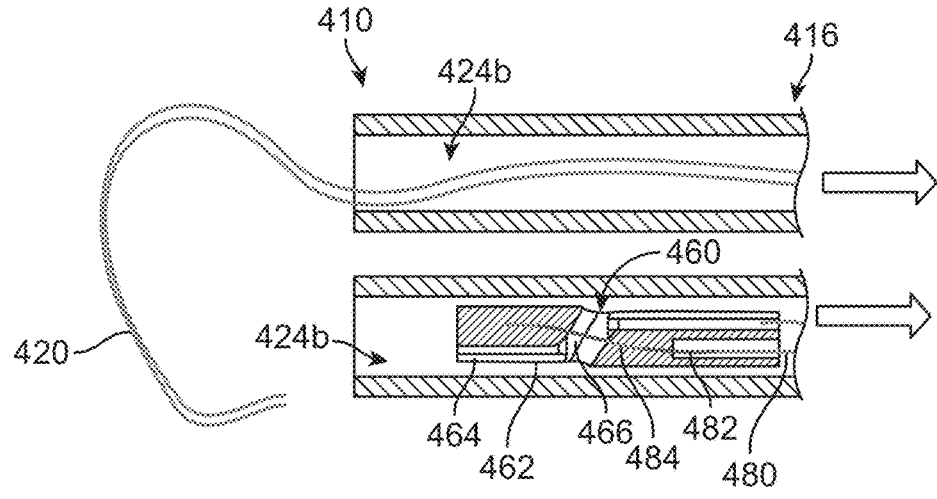
FIG. 9B is a partial, schematic illustration of the delivery device of FIG. 9A after actuation of the cutting assembly.
Figure 9C:
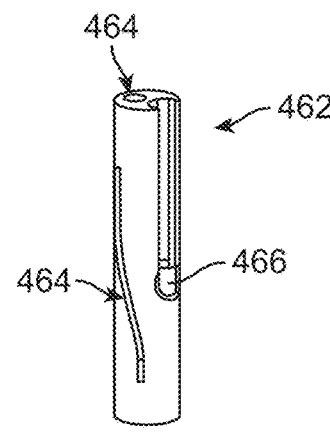
FIG. 9C is a side view of a blade holder of the cutting assembly of FIGS. 9A-9B.

Turning now to FIGS. 9A-9C, which schematically illustrate aspects of yet another embodiment of a delivery device 410 that is identical to delivery device 10 unless explicitly stated. The delivery device 410 has a shaft assembly 416 including at least two lumens 424a, 424b as well as a cutting assembly 460 positioned within the second lumen 424b. Only select components of the delivery device 410 are shown in FIGS. 9A-9C. It will be understood that the delivery device 410 can otherwise be configured and operate similar to the delivery device 10 of FIG. 1, for example. At least one tension member 420 of the type disclosed above (generally referenced) extends from a handle assembly (not shown, e.g., handle assembly 18 of FIG. 1) through the first lumen 424a, around the stented prosthesis (not shown) and then through a first channel 464a in a blade holder 462 of the cutting assembly 460 and then down through the second lumen 424b to the handle assembly. Therefore, both ends of the tension member 420 can optionally be tensioned (i.e. pulled proximally) to provide even crimping of the stented prosthesis.

The cutting assembly 460 further includes a flexible blade 482 that is positioned within a second channel 464 of the blade holder 462. The channel 464 can include a jog 466 angled with respect to a center axis of the second lumen 424b. In one example embodiment, the blade 482 is a circular blade defining an aperture 484. In such embodiments, at least one tension member 420 is threaded through the aperture 484 so that upon proximal retraction of the circular blade 482, the tension member(s) 420 are brought into contact with the circular blade 482, thus effectively severing each tension member 420 so that the tension member(s) 420 can be withdrawn from around the stented prosthesis and the patient after deployment of the stented prosthesis. Movement or actuation of the circular blade 482 can be controlled in a variety of ways. For example, the circular blade 482 can be connected to a handle actuator 480 or the like that extends through the second lumen 424b and is actuated by the handle assembly (i.e. the handle actuator 480 of this embodiment can be configured in the way disclosed with respect to other embodiments).

Referring now also to FIGS. 10A-11, which schematically illustrate select portions of yet another embodiment of a delivery device 510 that is identical to delivery device 10 unless explicitly stated. The delivery device 510 has a shaft assembly 516 with first and second lumens 524a, 524b as well as a cutting assembly 560 positioned in the second lumen 524b. At least one tension member 520 of the type disclosed above (generally referenced) extends from a handle assembly (not shown, e.g., handle assembly 18 of FIG. 1) through the first lumen 524a, around the stented prosthesis (not shown) and then through an aperture 564 in a holder 562 of the cutting assembly 560 and then back down through the first lumen 524a to the handle assembly. The cutting assembly 560 further includes a blade support 580 positioned within the second lumen 524b having a blade 582 at a distal end thereof and positioned such that the blade 582 extends out of the second lumen 524b. Upon proximal retraction of the holder 562 within the blade support 580, the tension member(s) 520 are brought into contact with the blade 582, thus effectively severing each tension member 520 so that each tension member 520 can be withdrawn from around the stented prosthesis and the patient after deployment of the stented prosthesis (not shown). Movement of the holder 562 can be controlled or actuated in a variety of ways. For example, the holder 562 can be connected to a pull member or the like 568 that extends through the second lumen 524b and is actuated by the handle assembly (i.e. the pull member 568 of this embodiment can be configured in the way disclosed with respect to other embodiments).

Figures 12A, 12B, 12C:
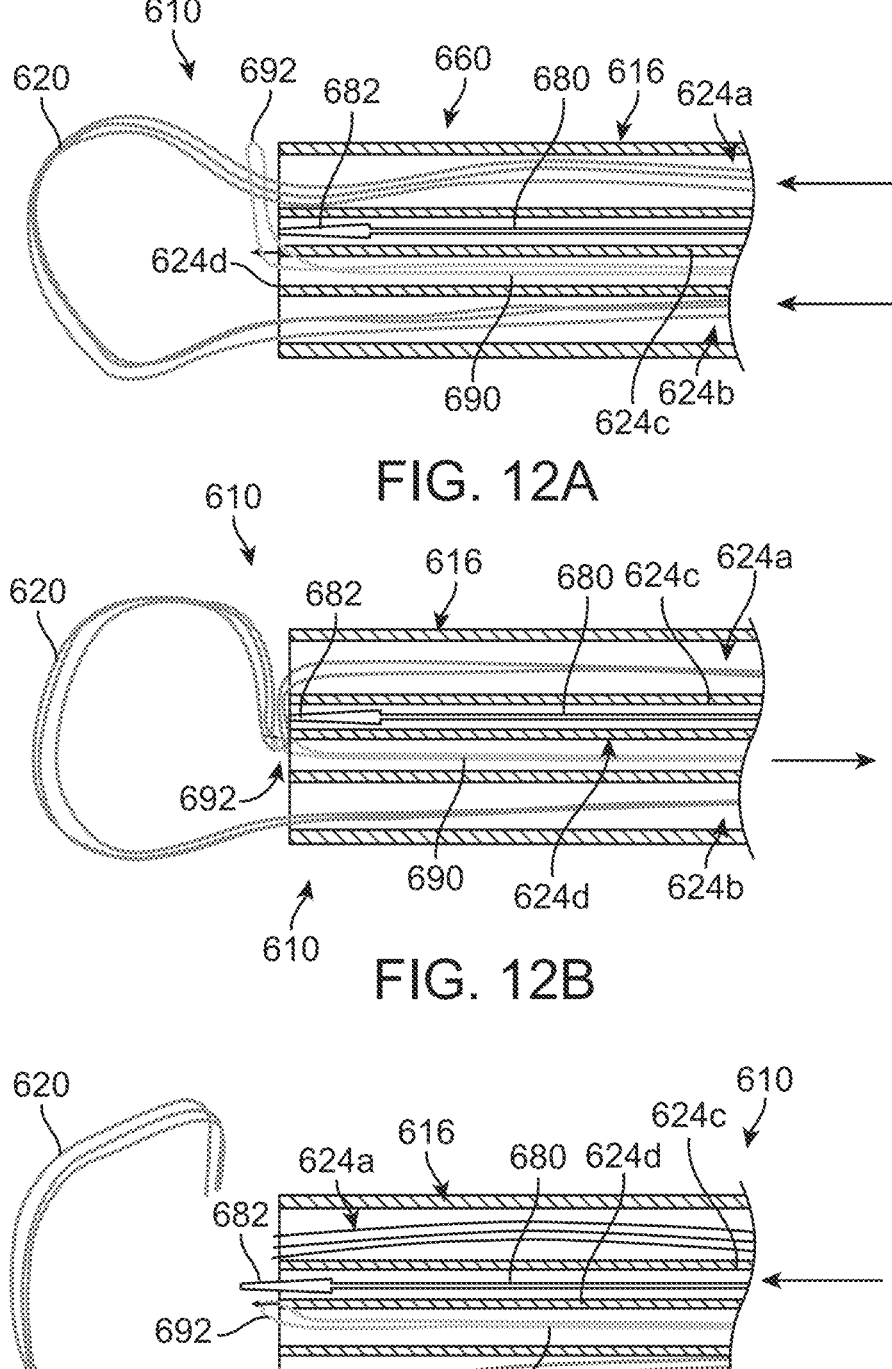
FIG. 12A is a partial, schematic illustration of an alternate delivery device prior to actuation of a cutting assembly.
FIG. 12B is a partial, schematic illustration of the delivery device of FIG. 12A after partial actuation of the cutting assembly.
FIG. 12C is a partial, schematic illustration of the delivery device of FIGS. 12A-12B after full actuation of the cutting assembly.

Referring now also to FIGS. 12A-12C, which schematically illustrate select portions of yet another embodiment of a delivery device 610 that is identical to delivery device 10 unless explicitly stated. The delivery device 610 has a shaft assembly 616 with four lumens 624a-d as well as a cutting assembly 660 positioned in the third lumen 624c. Similar to many prior disclosed embodiments, at least one tension member 620 (generally referenced) extends from a handle assembly (not shown, e.g., the handle assembly 18 of FIG. 1) through the first lumen 624a, around the stented prosthesis (not shown) and then then back down to the handle assembly through the second lumen 624b. The cutting assembly 660 includes a handle actuator 680 having a blade 682, which is slidably positioned in the third lumen 624c. A guide member 690, made of suture material or the like, is positioned in the fourth lumen 624d and includes a loop 692 extending out of the shaft assembly 616 through which the tension member(s) 620 are threaded. To tension each tension member 620, one or both ends each tension member 620 are proximally retracted, for example, with the handle assembly. To sever each tension member 620 after deployment of the stented prosthesis, the loop 692 is pulled proximally via the handle assembly or otherwise, to position each tension member 620 across an opening of the third lumen 624c (FIG. 12B). Then, the blade 682 can be distally advanced via the handle actuator 680 to sever each tension member 620 (FIG. 12C). The handle actuator 680 can be controlled via the handle assembly or otherwise.

Figure 13A:
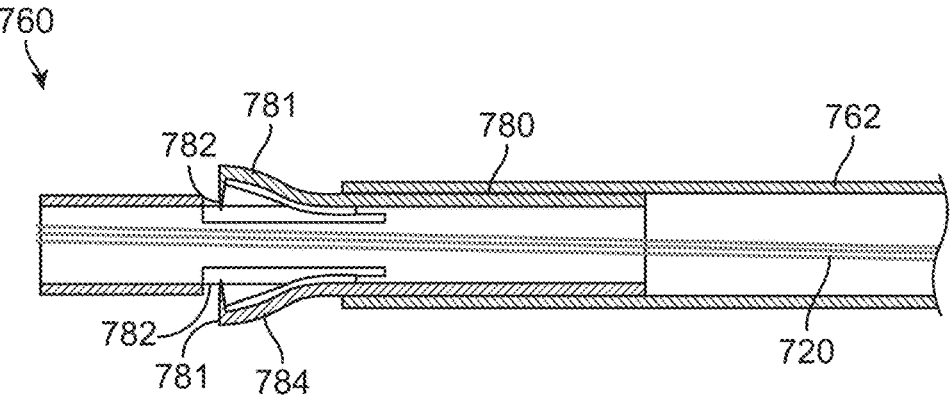
FIG. 13A is a partial, schematic illustration of an alternate cutting assembly prior to actuation of a cutting assembly.
Figure 13B:
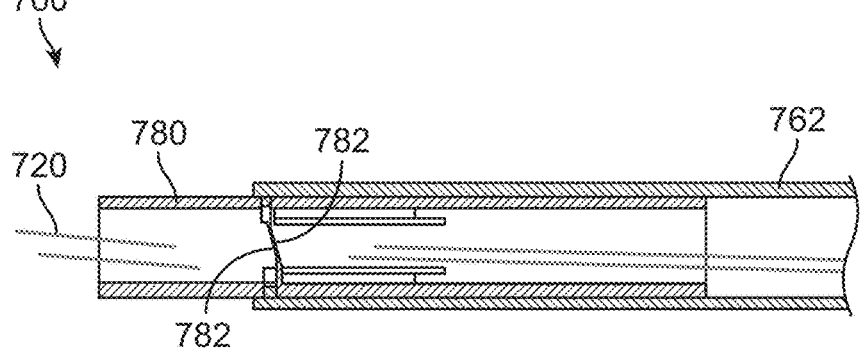
FIG. 13B is a partial, schematic illustration of the cutting assembly of FIG. 13A after actuation of the cutting assembly.
Figure 14:
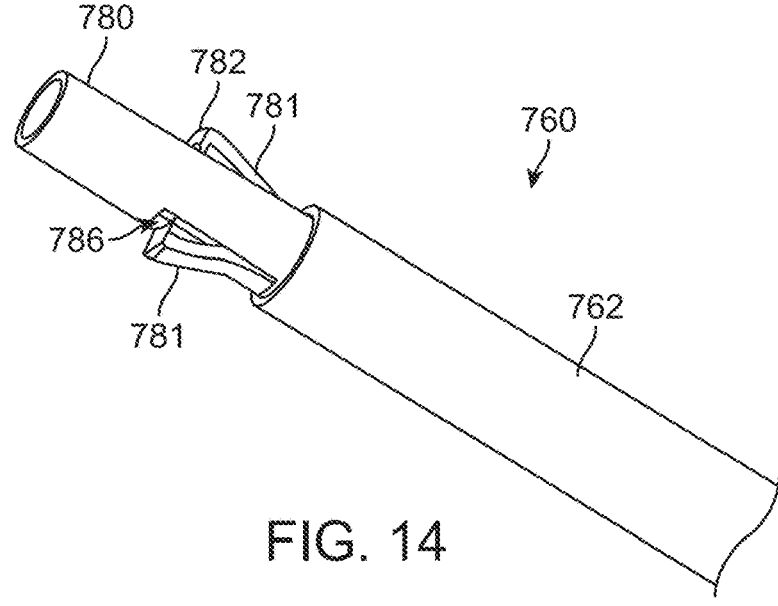
FIG. 14 is a partial, perspective view of the cutting assembly of FIGS. 13A-13B.

Referring now also to FIGS. 13A-14 which illustrate select portions of another cutting assembly 760 that can be incorporated into any of the shaft assemblies of delivery devices disclosed herein. In this embodiment, the cutting assembly 760 includes a blade holder 762 that is inserted and secured within a lumen of a shaft assembly (not shown, see the shaft assemblies disclosed above). The cutting assembly 760 further includes an inner tube 780 through which one or more tension members 720 (generally referenced) of the type previously disclosed are routed. The inner tube 780 includes a plurality of flexible blade assemblies 781 each having a blade 782 and a ramped surface or arms 784 protruding from the inner tube 780. In one example embodiment, the inner tube 780 includes two flexible blade assemblies 781 positioned approximately 180 degrees from one another around the circumference of the inner tube 780. In a first state prior to actuation, each blade assembly 781 extends outwardly from the inner tube 780 and the blade 782 is arranged generally perpendicular to a longitudinal axis of the inner tube 780. To sever the tension member(s) 720, the inner tube 780 is drawn proximally such that the flexible blade assemblies 781 are compressed against the blade holder 762 to extend through respective windows 786 in the inner tube 780 so that the blades 782 to sever the tension member(s) 720 routed through the inner tube 780. Selective movement or actuation of the inner tube 780 can be achieved in many ways. For example, the inner tube 780 can be connected to a handle actuator (i.e. pin) or the like (not shown) that extends through the second lumen 724b and is actuated by a handle assembly (e.g., the handle assembly 18 of FIG. 1).

Figure 15A:
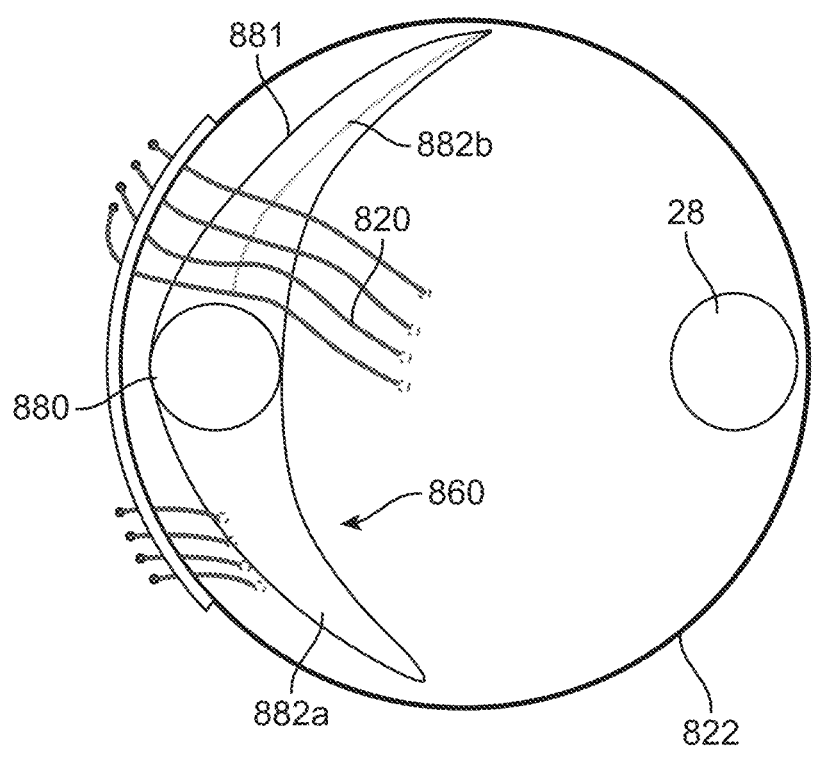
FIG. 15A is a partial, schematic cross-sectional view of a distal portion of a shaft assembly through which a plurality of tension members are routed; wherein a cutting member is positioned within the distal portion.
Figure 15B:
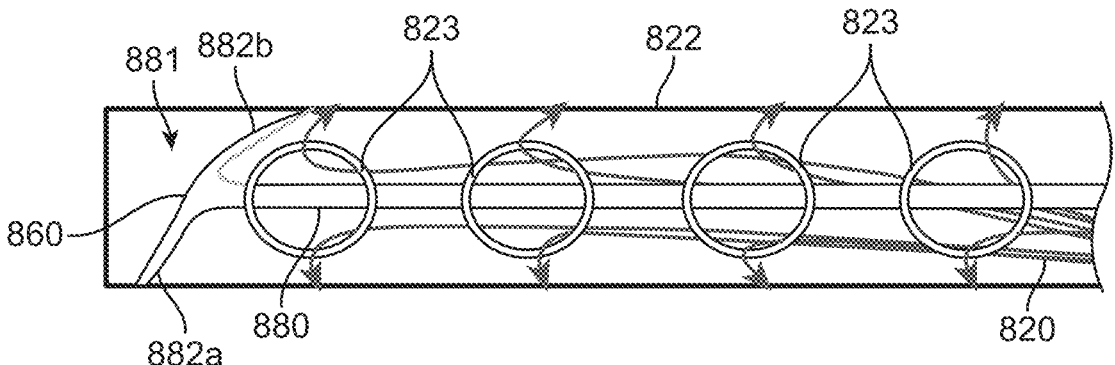
FIG. 15B is a partial, schematic top view of the distal portion of FIG. 15A (shown as transparent for ease of illustration).

Turning now also to FIGS. 15A-15B, which schematically illustrate a further embodiment of a distal portion 822 that can be incorporated into any of the delivery devices disclosed herein (e.g., the delivery device of FIG. 1). In this example embodiment, the distal portion 822 includes windows or apertures 823 (e.g., four) through which respective tension members 820 (generally referenced) are routed from a location proximal the distal portion 822 (e.g., a handle assembly) to around the stented prosthesis (not shown) so that the stented prosthesis can be compressed and expanded via adjusting the tension in the tension members 820. The tension members 820 can be of the type disclosed above. In alternate embodiments, a different number of windows 823 and tension members 820 can be utilized, as desired. After allowing the stented prosthesis to expand, the tension members 820 can be released from the stented prosthesis with a cutting assembly 860. The cutting assembly 860 can include a pin 880 having a head 881. The head 881 can generally span a diameter of the distal portion 822 and can include two portions, one portion being a blunt edge 882*a* and the other opposing portion being a blade 882*b*. During actuation, the blunt and blade edges 882*a*, 882*b* are drawn over the tension members 820 as the cutting assembly 860 (via the pin 862) is drawn proximally. The blunt edge 882*a* passes over and does not damage the tension members 820 while the blade edge 882*b* is arranged and configured to sever each tension member 820 as the blade edge 882*b* contacts each tension member 820. Each tension member 820 is only severed at one location so that the tension members 820 can subsequently be proximally pulled and withdrawn from the patient along with the delivery device.

Figure 16A:
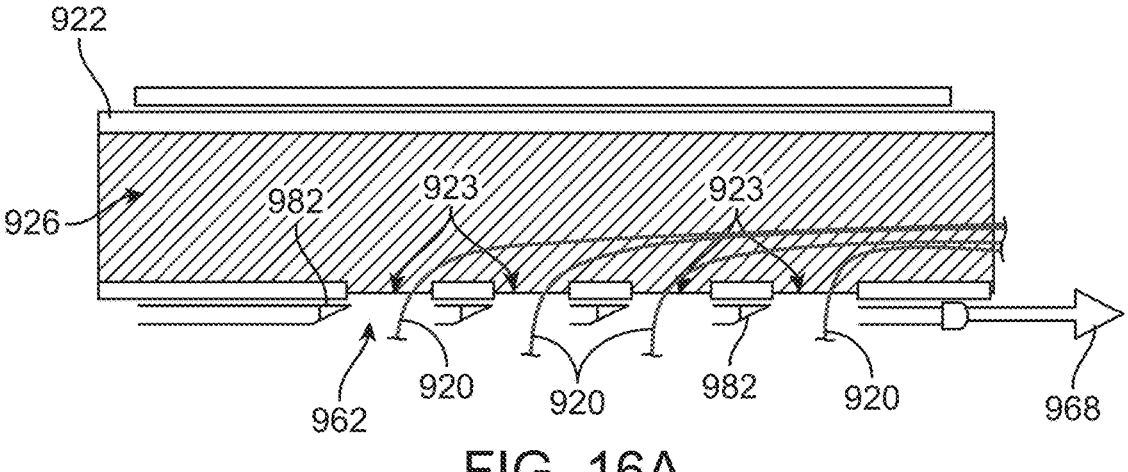
FIGS. 16A-16C are partial, schematic illustrations of an alternate distal portion of a shaft assembly over which a cutting assembly in the form of a sheath is positioned.
Figure 16B:
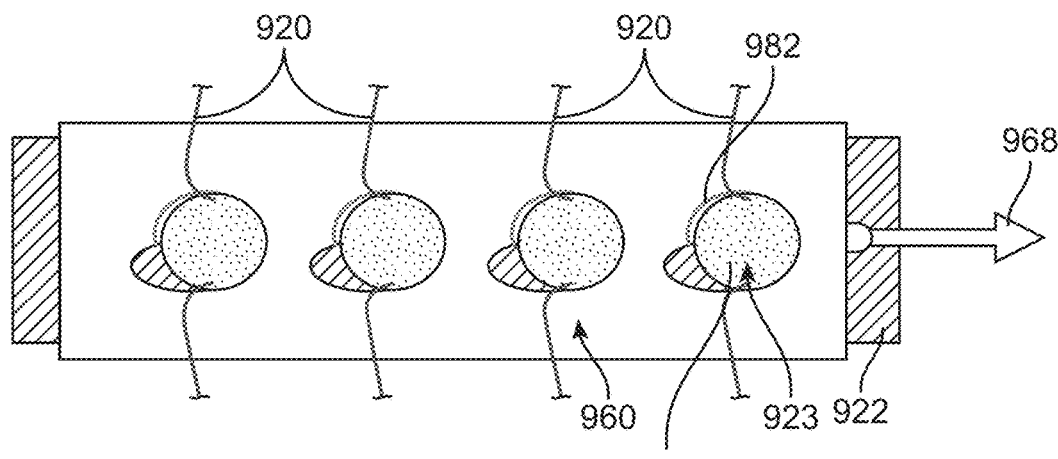
Figure 16C:
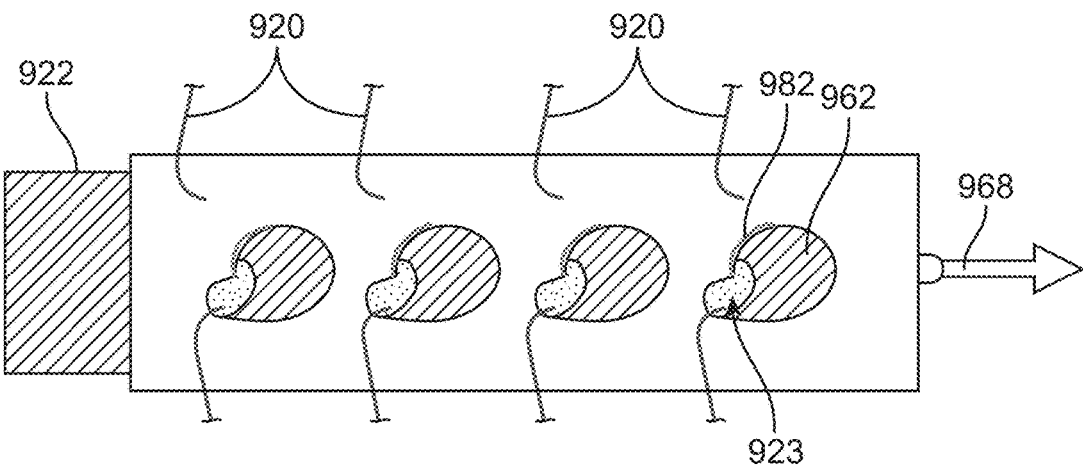

Referring now in addition to FIGS. 16A-16C, which schematically illustrate select components of yet another distal portion 922 that can be incorporated into any of the delivery devices disclosed herein (e.g., the delivery device 10 of FIG. 1). The distal portion 922 includes a plurality of windows 923 through which one or more respective tension members 920 can be routed as each tension member 920 extends from within a lumen 926 of the distal portion 922 out of one window 923, around the stented prosthesis (not shown) and then back through the respective window 923 and into the lumen 926 in the direction of the handle assembly (e.g., the handle assembly 18) or similar actuating device for controlling the tension in each tension member 920. The distal portion 922 can further include a cutting assembly 960 in the form of a sleeve including a plurality of apertures 962 that correspond in position with the windows 923 of the distal portion 922. Each sleeve aperture 962 includes a blade 982 arranged and configured such that movement of the sleeve 960 draws the blade 982 over the tension members 920, effectively severing the tension members 920. The cutting assembly 960 can be actuated with a pull pin 968 or the like that can optionally be controlled by the handle assembly. In various embodiments, the blade 982 can be positioned in the respective aperture 962 so that each tension member 920 is only severed in one location. In this configuration, the tension members 920 are still connected to the delivery device (e.g., at the handle assembly), which can then proximally withdraw the tension members 920 for removal along with the delivery device after deployment of the stented prosthesis. As shown, the cutting assembly 960 can be configured such that proximal movement of the cutting assembly 960 severs the tension members 920. It will be understood that the cutting assembly 960 can be configured such that movement of the cutting assembly 960 in other directions with respect to the distal portion 922 will sever the tension members 920.

Figure 17A:
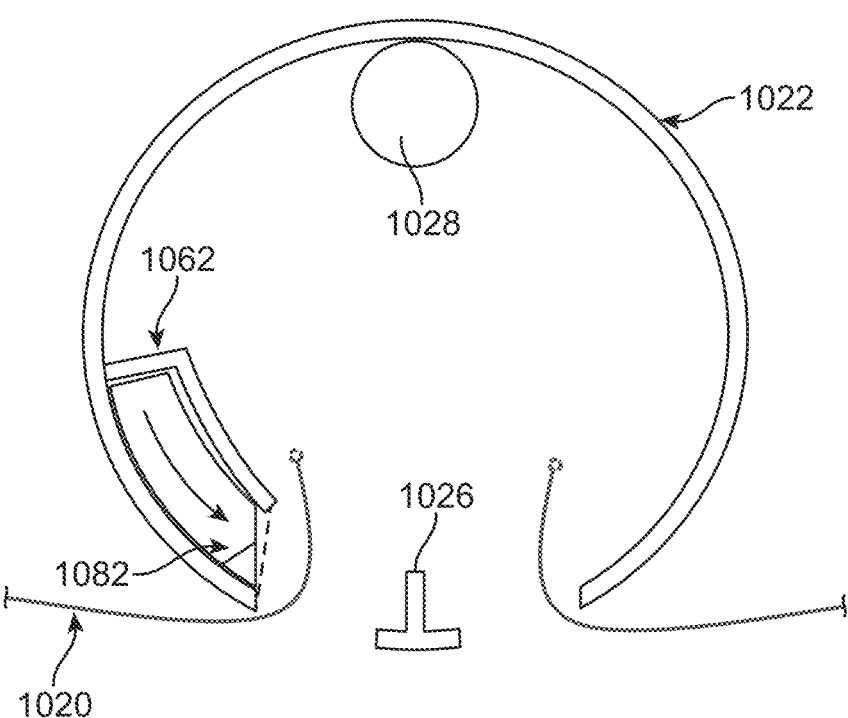
FIG. 17A is a partial, schematic cross-sectional view of an alternate distal portion of a shaft assembly in which a cutting assembly is positioned prior to actuation of the cutting assembly.
Figure 17B:
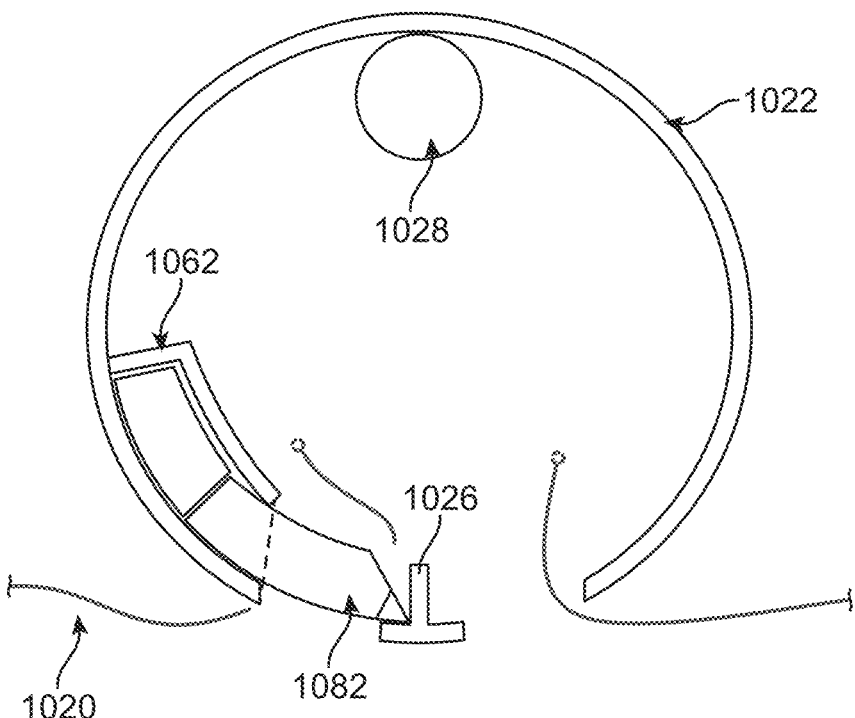
FIG. 17B is a partial, schematic cross-sectional view of the distal portion of FIG. 17A in which the cutting assembly has been actuated to sever one or more tension members provided (only one tension member is visible).
Figure 17D:
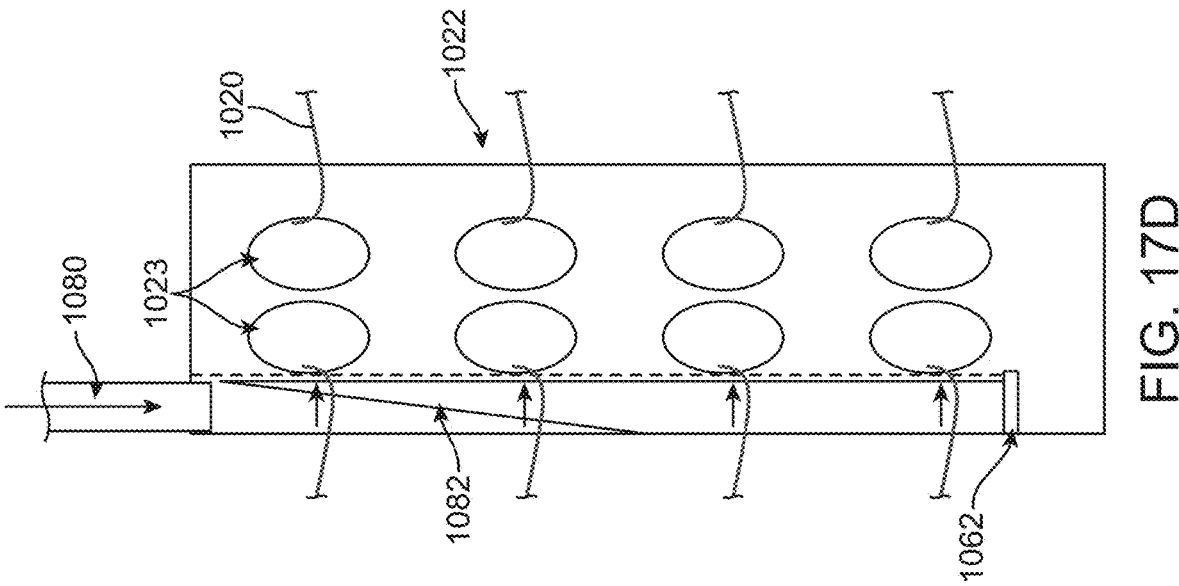
FIG. 17D is a schematic front view of the distal portion of FIGS. 17A-17C.
Figure 17C:
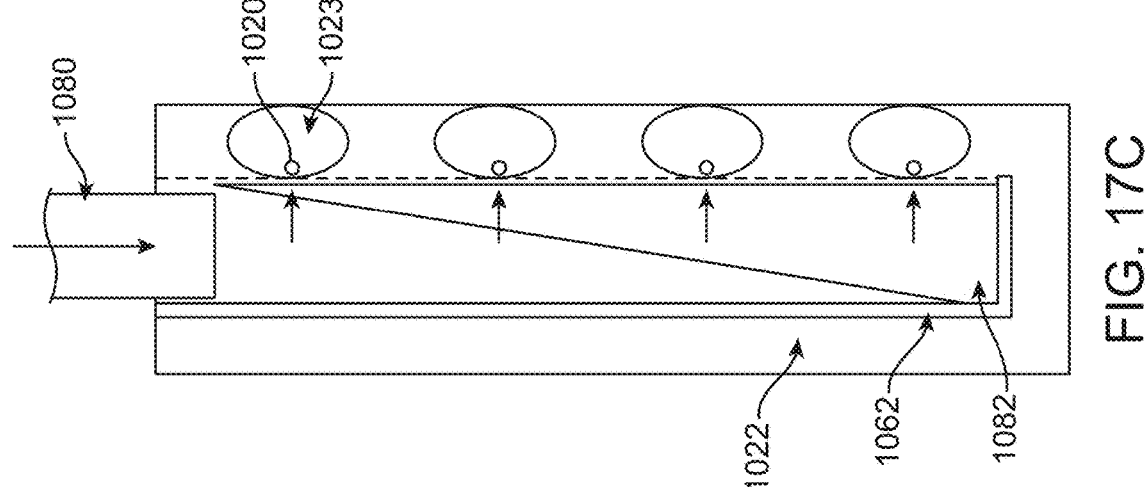
FIG. 17C is a schematic side view of the distal portion of FIGS. 17A-17B (having certain components shown as transparent for ease of illustration).
Figures 18A, 18B, 18C, 18D, 18E:
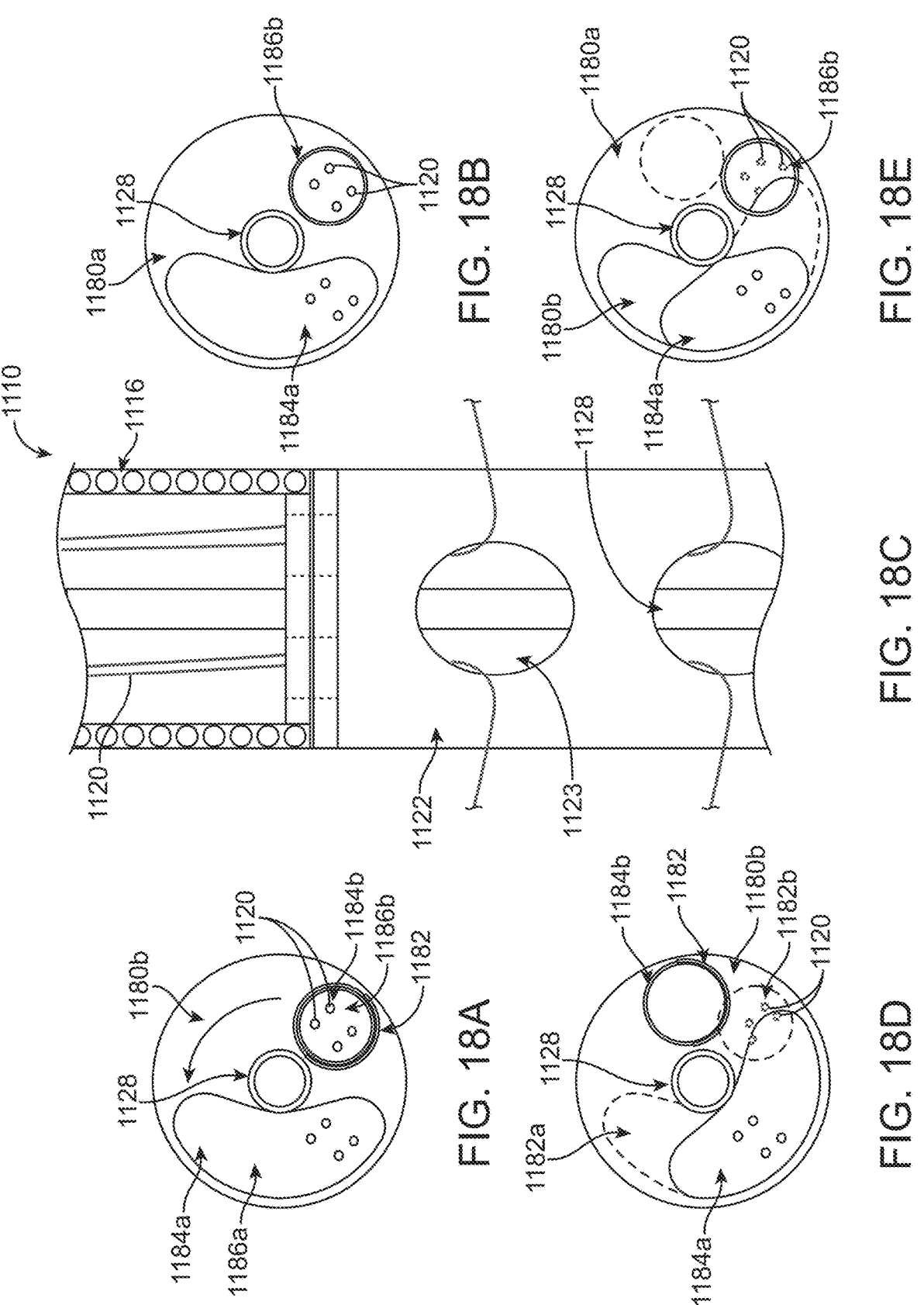
FIGS. 18A-18C schematically illustrate an alternate cutting assembly prior to actuation of the cutting assembly.
FIGS. 18D-18E schematically illustrate actuation of the cutting assembly of FIGS. 18A-18C.

Referring now also to FIGS. 17A-17D, which illustrate select components of an alternate distal portion 1022 that can be incorporated into any of the delivery devices disclosed herein, such as the delivery device 10 of FIG. 1. The distal portion 1022 can include a plurality of windows 1023 through which one or more tension members 1020 extend to compressively retain the stented prosthesis (not shown). In some embodiments, the distal portion 1022 includes one pair of windows 1023 for each tension member 1020 provided, as shown. FIGS. 17A-17B are cross-sectional views of the distal portion 1022 in which a guide wire 1028 is located, along with a cutting assembly 1060 including a curved blade 1082 slidably positioned within a confinement frame 1062. The blade 1082 can slide within the confinement frame 1062 and movement of the blade 1082 is further limited by a separator 1026, which also separates first and second ends of each tension member 1020 (only one tension member 1020 is visible in FIGS. 17A-17B). Once the stented prosthesis is expanded at the target site and ready for full deployment, the cutting assembly 1060 can be actuated from the position of FIG. 17A to the position of 17B in which the blade 1082 moves along a circumference of the distal portion 1022 to sever each tension member 1020 once. Actuation of the blade 1082 can be achieved with a pin 1080, for example, which can be pushed distally (via a handle assembly or otherwise, e.g., the handle assembly 18 of FIG. 1), to displace the blade 1082 toward the windows 1023 until the blade 1082 contacts the separator 1026. The delivery device in which the distal portion 1022 is incorporated can be configured and operate similar to the delivery device 10 in all other respects.

Referring now also to FIGS. 18A-18E, which illustrate select components of an alternate delivery device 1110 that can be largely similar to the delivery device 10 of FIG. 1 except as explicitly stated. The delivery device 1110 includes a torque shaft 1116, a distal portion 1122, a guide wire 1128. The torque shaft 1116 can be largely similar to the shaft assembly 16 but also be configured to rotate. In alternate embodiments, the torque shaft 1116 can be provided within a shaft assembly (e.g., the shaft assembly 16) or the like. The delivery device 1110 further includes a stationary disk 1180*a* and interface disk 1180*b* connected to the torque shaft 1116. In some embodiments, that stationary disk 1180*a* and interface disk 1180*b* are longitudinally positioned between the distal portion 1122 and the torque shaft 1116. The delivery device 1110 utilizes one or more tension members 1120 that can be routed from a handle assembly (not shown, e.g., the handle assembly 18 of FIG. 1), through the torque shaft 1116, through the distal portion 1122 and out of an aperture 1123 in the distal portion 1122 to circumscribe a stented prosthesis (not shown). The tension members 1120 are then routed from the stented prosthesis back through the respective aperture 1123 and to the handle assembly. The tension members 1120 can be of the type described above with respect to other embodiments.

Each of the stationary and the interface disks 1180*a*, 1180*b* include respective apertures 1184*a-b*, 1186*a-b* for receiving each tension member 1120. One set of apertures 1184*a*, 1186*a* receives the tension members 1120 as they are routed to the distal portion 1122 and one set of apertures 1184*b*, 1186*b* receives the tension members 1120 as the tension members 1120 are routed from the distal portion 1122 toward the handle assembly or the like. The rotating interface disk 1180*b* also includes a blade 1182 positioned around at least part of one aperture 1186*a* (e.g., the aperture 1186*a* receiving the tension members 1120 as they are routed to the distal portion 1122). Once the stented prosthesis is delivered to a target site and expanded, the tension members 1120 can be released from around the stented prosthesis by actuating or rotating the torque shaft 1116, via the handle assembly or otherwise, to correspondingly rotate the attached interface disk 1180*b* until the blade 1182 passes through and severs the tension members 1120 positioned within the first set of apertures 1184*a*, 1186*a*. After severing, the tension members 1120, the tension members 1120 can be pulled from the stented prosthesis and proximally withdrawn from the patient along with the rest of the delivery device.

Figure 19A:
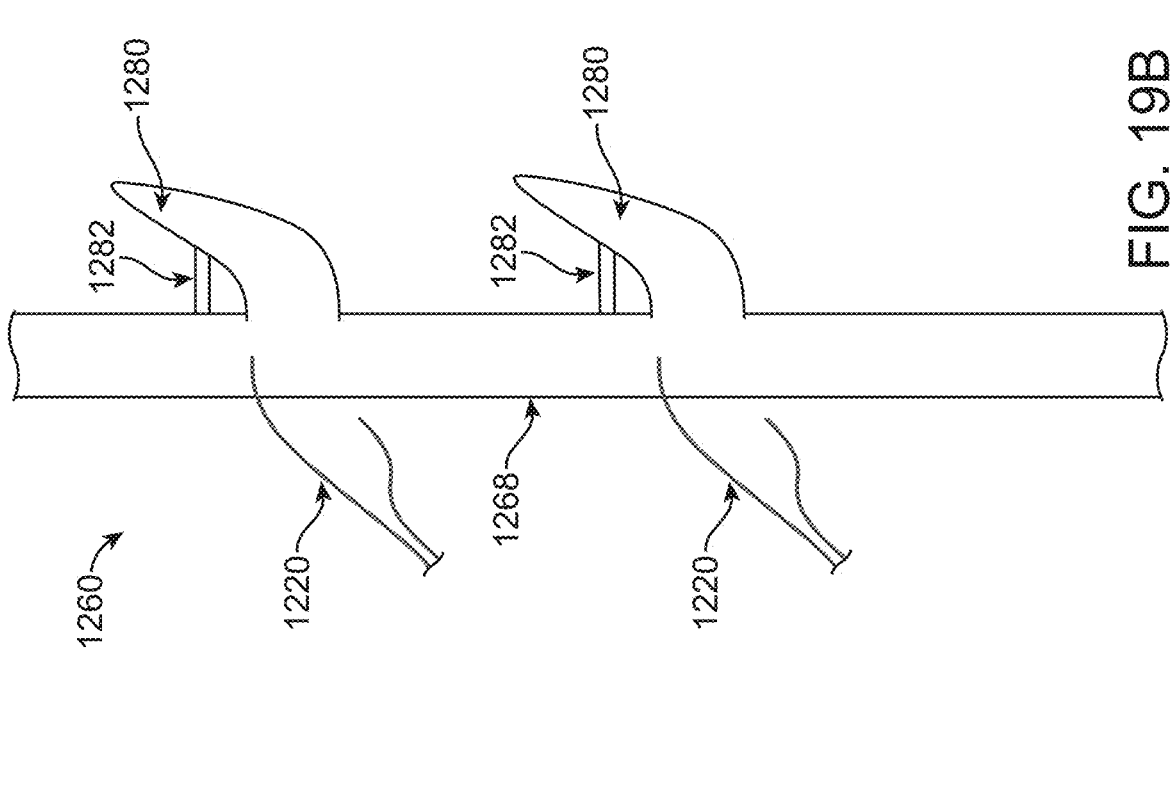
FIG. 19A is a partial, schematic illustration of an alternate cutting assembly prior to actuation of the cutting assembly.
Figure 19B:
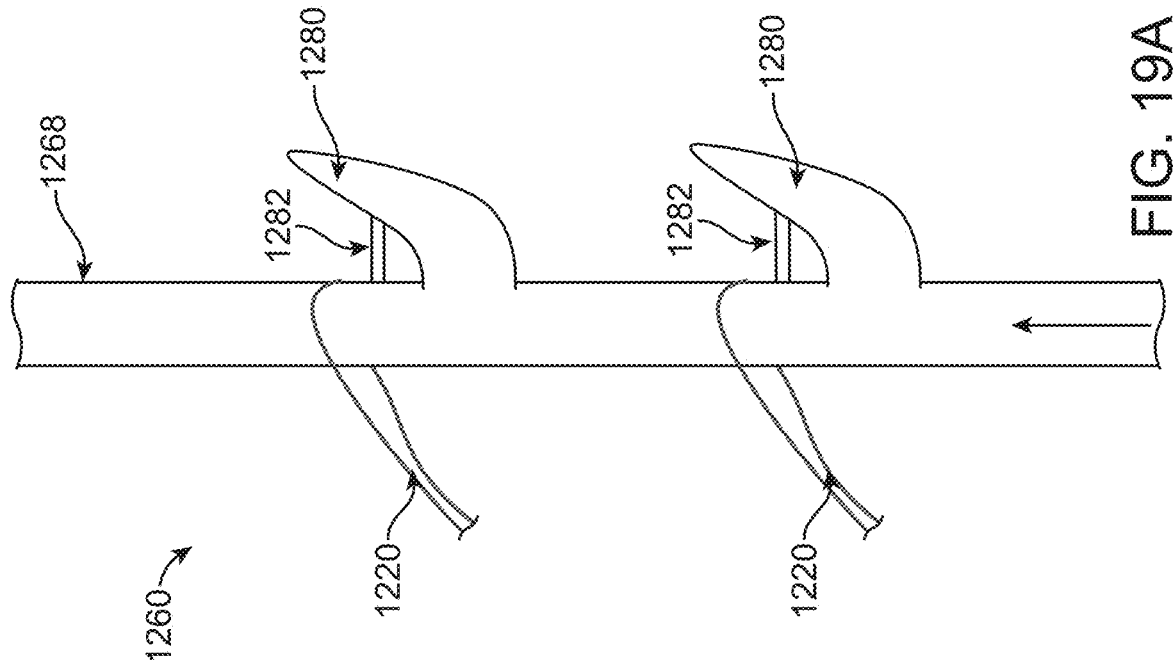
FIG. 19B is a partial, schematic illustration of the cutting assembly of FIG. 19A after actuation of the cutting assembly.
Figures 20A, 20B:
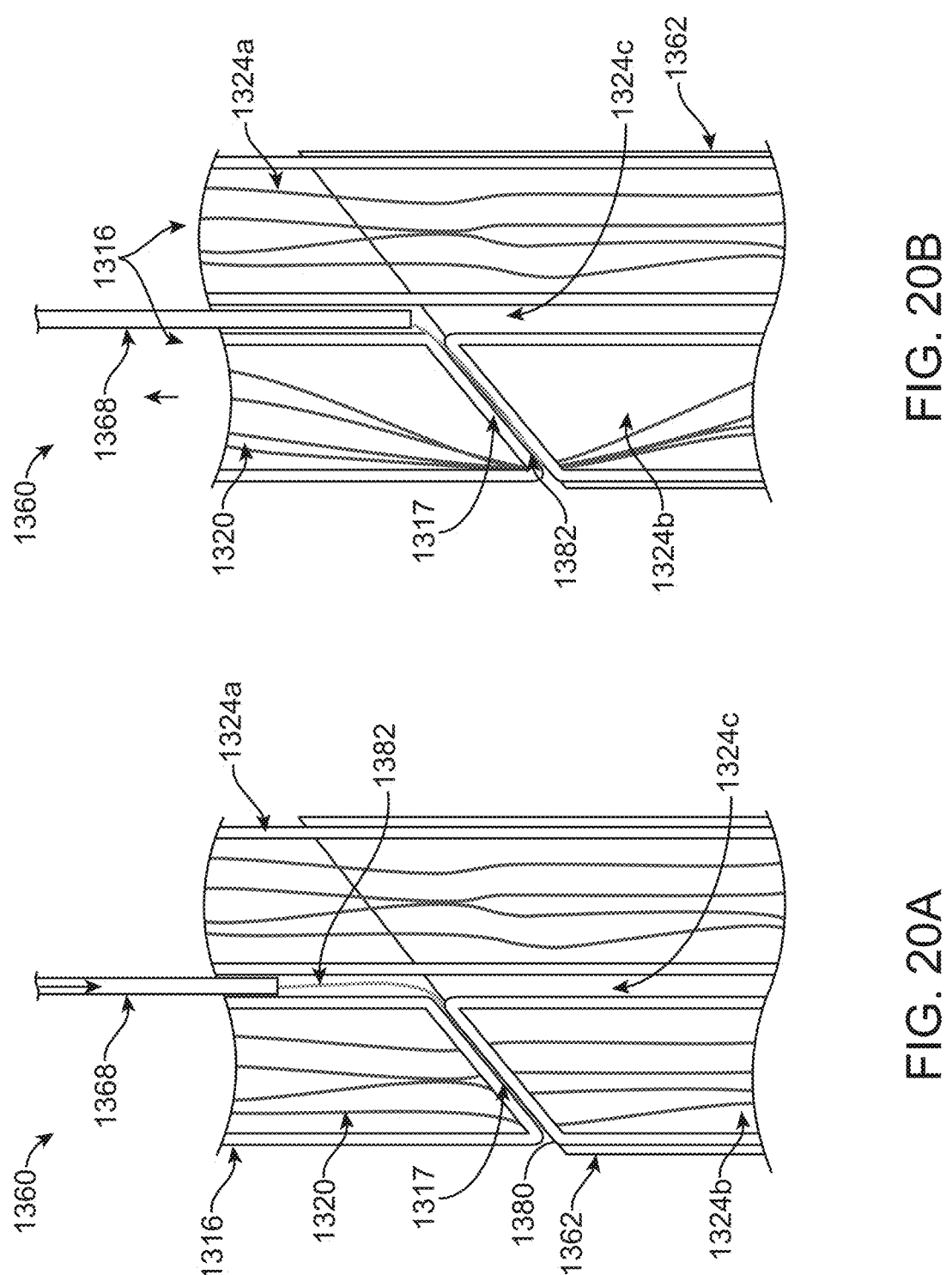
FIG. 20A is a partial, schematic cross-sectional view of an alternate shaft assembly and a cutting assembly prior to actuation of the cutting assembly.
FIG. 20B is a partial, schematic cross-sectional view of the shaft assembly and cutting assembly of FIG. 20A after actuation of the cutting assembly.
Figure 20C:
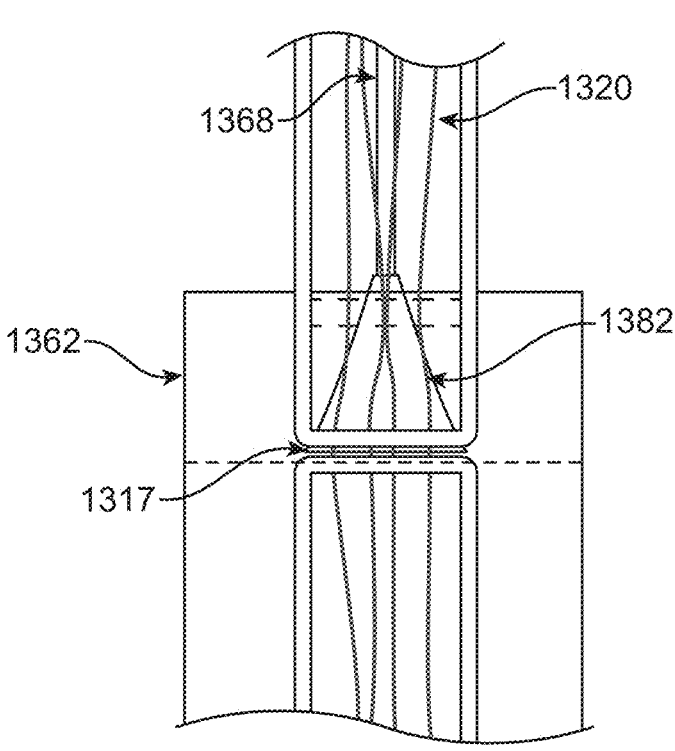
FIG. 20C is a partial, schematic cross-sectional side view of the shaft assembly and cutting assembly of FIGS. 20A-20B.
Figure 20D:
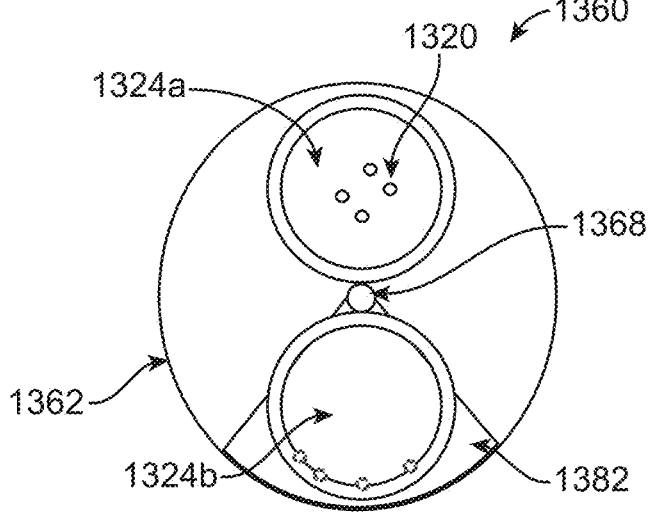
FIG. 20D is a partial, schematic cross-sectional top view of the shaft assembly and cutting assembly of FIGS. 20A-20C.

Referring now in addition to FIGS. 19A-19B, which schematically illustrate an alternate cutting assembly 1260 that can be incorporated into any of the delivery devices disclosed herein, for example, by inserting the cutting assembly 1260 within a shaft assembly or distal portion and actuated with a handle assembly or the like (see also, in particular, FIG. 1 and related disclosure). In this embodiment, the cutting assembly 1260 includes a pin 1268 having one or more barbs 1280 angled in a distal direction. One or more elongate tension members 1220 of the type disclosed above are wound around the pin 1268, distal to one respective barb 1280 such that proximal retraction of the pin 1268, via a handle assembly or otherwise, draws a blade 1282 of each barb 1280 through the respective tension member(s) 1220 effectively severing the tension member(s) 1220 for release of the tension member(s) 1220 from a deployed stented prosthesis as generally described above.

FIGS. 20A-20D schematically illustrate an alternate embodiment of a cutting assembly 1360 that can be incorporated into a shaft assembly of any of the delivery devices disclosed herein utilizing a plurality of elongate tension members 1320 (generally referenced), as well as elements arranged and configured similar to other embodiments disclosed herein (e.g., see FIG. 1 and related disclosure). The shaft assembly 1316 of this embodiment can include three or more lumens 1326*a*, 1326*b*, 1326*c*. Each tension member 1320 is threaded from the handle assembly (e.g., handle assembly 18 of FIG. 1) through the first lumen 1324*a*, around the stented prosthesis (not shown), and then then back proximally through the second lumen 1324*b* to a handle assembly or the like (not shown). The third lumen 1326*c* can be centrally located with respect to the shaft assembly 1316 and is provided, at least in part, to receive a flexible cutting blade 1382. A jog 1317 may be provided in the shaft assembly 1316 to interconnect the second and third lumens 1324*b*, 1326*c*. In addition, a blade guide 1362 can be provided so that as the blade 1382 is distally advanced, the blade 1382 contacts the blade guide 1362 and then is directed through the jog 1317 to enter the second lumen 1324*b* and sever each tension member 1320 within the second lumen 1324*b*. In some embodiments, the blade guide 1362 has an edge 1380 that is angled so that the blade 1382 is directed to cut across the second lumen 1324*b* diagonally. In this way, the tension member(s) 1320 are pinned between a wall of the second lumen 1324*b* and the blade 1382. The tension member(s) 1320 can further be tensioned at this time, via the handle assembly or otherwise, to assist in severing the tension member(s) 1320 at the contact point of the blade 1382. The blade 1382 can be actuated in a variety of ways. In one example embodiment, movement of the blade 1382 is controlled with a pin 1368, which can be controlled by the handle assembly.

Embodiments of the disclosure include a delivery device for delivering a stented prosthesis to a target site; the delivery device comprising: at least one elongate tension member that can compressively retain the stented prosthesis to the delivery device; and a shaft assembly having a lumen and a cutting assembly positioned within the lumen; wherein the cutting assembly includes a blade that is configured to selectively sever the at least one elongate tension member. The disclosed delivery devices can include a flexible blade. In some embodiments, the cutting assembly includes a blade holder defining a jog through which the blade can travel. In various embodiments, the delivery device further includes a handle assembly and the cutting assembly actuates movement of the cutting assembly. Each of the elongate tension members can include first and second ends; wherein the first and second ends are connected to the cutting assembly. Each of the elongate tension members can be interconnected with a loop that can be severed by the cutting assembly. In some embodiments, the blade is a circular blade circumscribing an aperture in the cutting assembly. In various embodiments, the elongate tension members are positioned within an aperture prior to being severed. In some embodiments, the cutting assembly can move within the lumen. In various embodiments, the cutting assembly includes a pin through which the elongate tension members are threaded and also a cutting blade that is fixed to the lumen; wherein the pin can move with respect to the cutting blade. In some embodiments, the cutting assembly includes a cutting blade and a cord looped around the elongate tension members that is configured to draw the elongate tension members toward the cutting blade. In some embodiments, the cutting blade can be actuated to extend out of the lumen to sever the elongate tension members. In various embodiments, the cutting assembly includes a pair of resilient blades extending out of a hollow shaft; wherein the blades are configured to be actuated by compressing the blades against the hollow shaft. In some embodiments, the shaft is hollow and the elongate tension members are threaded through the hollow shaft. In some embodiments, the delivery device has a loaded state in which a stented prosthetic heart valve is loaded thereto; wherein the blade is positioned distal to the elongate tension members in the loaded state. In various embodiments the cutting assembly includes a pull pin positioned within the lumen; wherein the blade is secured to the pull pin. In some embodiments, the cutting assembly includes a sleeve having a plurality of windows; wherein the blade is positioned at an edge of at least one of the plurality of windows; wherein the sleeve can move along the shaft assembly. In some embodiments, the cutting assembly includes a plurality of blades such that each window edge includes blade. In some embodiments, the blade can travel along a path defined by an inner diameter of the lumen. In some embodiments, movement of the blade is restricted by a separator. In some embodiments, the blade rotates within the shaft assembly. In some embodiments, the blade rotates around a central axis of the shaft assembly. In various embodiments, the cutting assembly includes a torque shaft, a stationary disk and an interface disk; wherein the blade is positioned on an edge of an aperture in one of the stationary disk or the interface disk. In some embodiments, the cutting assembly includes a pull pin including a plurality of protrusions on which one blade is positioned; the protrusions being arranged and configured to engage and sever the elongate tension members at the blades. In some embodiments, the cutting assembly includes a pull pin and the blade extends from a distal end of the pull pin; wherein actuation of the blade is accomplished with movement of the pull pin. In some embodiments, the shaft assembly includes first, second and third lumens; wherein the at least one tension member is routed through the first and second lumens and the cutting assembly is at least partially positioned within the third lumen; wherein a gap interconnects the second and third lumens and a blade of the cutting assembly can travel through the gap to the second lumen.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthesis to a target site, the delivery device comprising:

a shaft assembly comprising a lumen;

a cutting assembly at least partially disposed within the lumen of the shaft assembly, the cutting assembly comprising a blade; and an elongate tension member attached to the cutting assembly, wherein the cutting assembly is configured to be moved proximally within the lumen of the shaft assembly to pull the elongate tension member to compress the stented prosthesis with the elongate tension member when the elongate tension member is attached to the cutting assembly, the cutting assembly is further configured to move distally within the lumen to release compression applied by the elongate tension member to the stented prosthesis so that the stented prosthesis expands for deployment, and wherein the blade of the cutting assembly is configured to selectively sever the elongate tension member to selectively detach the elongate tension member from the cutting assembly.

2. The delivery device of claim 1, wherein the cutting assembly comprises a blade holder comprising an inner passage movably supporting the blade, wherein the elongate tension member is attached to the blade holder, and one of the blade and the blade holder is configured to move relative to the other of the blade and the blade holder to selectively sever the elongate tension member to selectively detach the elongate tension member from the cutting assembly.

3. The delivery device of claim 2, further comprising a pull member attached to the blade holder.

4. The delivery device of claim 2, wherein the blade holder comprises a first aperture, the elongate tension member is threaded through the first aperture to attach the elongate tension member to the blade holder, and the blade is positioned distally from the first aperture when the elongate tension member is attached to the cutting assembly.

5. The delivery device of claim 1, wherein the blade holder comprises a first aperture and a second aperture proximally spaced from the first aperture, and the elongate tension member is threaded through the first aperture.

6. The delivery device of claim 5, further comprising a pull member threaded through the second aperture of the blade holder.

7. The delivery device of claim 1, wherein the lumen comprises a first lumen and a second lumen, wherein the cutting assembly is at least partially disposed within the second lumen.

8. The delivery device of claim 7, wherein the cutting assembly comprises a blade holder comprising an inner passage movably supporting the blade, wherein the elongate tension member is attached to the blade holder, and one of the blade and the blade holder is configured to move relative to the other of the blade and the blade holder to selectively sever the elongate tension member to selectively detach the elongate tension member from the blade holder.

9. The delivery device of claim 8, further comprising a pull member attached to the blade holder.

10. The delivery device of claim 8, wherein the blade holder comprises a first aperture and a second aperture proximally spaced from the first aperture, and the elongate tension member is threaded through the first aperture.

11. The delivery device of claim 10, further comprising a pull member threaded through the second aperture of the blade holder.

12. The delivery device of claim 7, wherein the elongate tension member includes a first portion extending through a distal opening of the first lumen and a second portion extending through a distal opening of the second lumen, wherein the second portion of the elongate tension member is attached to the cutting assembly.

13. The delivery device of claim 12, wherein the cutting assembly comprises a blade holder comprising an inner passage movably supporting the blade, wherein the second portion of the elongate tension member is attached to the blade holder, and one of the blade and the blade holder is configured to move relative to the other of the blade and the blade holder to selectively sever the second portion of the elongate tension member to selectively detach the elongate tension member from the cutting assembly.

14. The delivery device of claim 13, further comprising a pull member attached to the blade holder.

15. The delivery device of claim 12, wherein the blade holder comprises a first aperture and a second aperture proximally spaced from the first aperture, and the second portion of the elongate tension member is threaded through the first aperture.

16. The delivery device of claim 15, further comprising a pull member threaded through the second aperture of the blade holder.

17. A delivery device for delivering a stented prosthesis to a target site, the delivery device comprising:

a shaft assembly comprising a first lumen and a second lumen;

a cutting assembly at least partially disposed within the second lumen, the cutting assembly comprising a blade and a blade holder comprising an inner passage movably supporting the blade; and an elongate tension member comprising a first portion extending through a distal opening of the first lumen and a second portion extending through a distal opening of the second lumen, wherein the second portion of the elongate tension member is attached to the blade holder, the cutting assembly is configured to be moved proximally within the second lumen of the shaft assembly to pull the elongate tension member to compress the stented prosthesis with the elongate tension member when the second portion of the elongate tension member is attached to the blade holder, the cutting assembly is further configured to move distally within the second lumen to release compression applied by the elongate tension member to the stented prosthesis so that the stented prosthesis expands for deployment, and wherein one of the blade and the blade holder is configured to move relative to the other of the blade and the blade holder to selectively sever the second portion of the elongate tension member to selectively detach the elongate tension member from the blade holder.

18. The delivery device of claim 17, further comprising a pull member attached to the blade holder.

19. The delivery device of claim 17, wherein the blade holder comprises a first aperture and a second aperture proximally spaced from the first aperture, the second portion of the elongate tension member is threaded through the first aperture, and a pull member threaded through the second aperture of the blade holder.

20. The delivery device of claim 17, wherein the blade holder comprises a first aperture, the second portion of the elongate tension member is threaded through the first aperture to attach the second portion of the elongate tension member to the blade holder, and the blade is positioned distally from the first aperture when the second portion of the elongate tension member is attached to the cutting 5 assembly.

* * * * *